(12) United States Patent
Okell et al.

(10) Patent No.: US 9,501,620 B2
(45) Date of Patent: Nov. 22, 2016

(54) QUANTIFICATION OF BLOOD VOLUME FLOW RATES FROM DYNAMIC ANGIOGRAPHY DATA

(71) Applicant: Isis Innovation Ltd., Oxford (GB)

(72) Inventors: Thomas Okell, Oxford (GB); Michael Chappell, Oxford (GB); Peter Jezzard, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 876 days.

(21) Appl. No.: 13/815,854

(22) Filed: Mar. 14, 2013

(65) Prior Publication Data
US 2013/0253895 A1    Sep. 26, 2013

Related U.S. Application Data

(60) Provisional application No. 61/685,598, filed on Mar. 20, 2012.

(51) Int. Cl.
G06F 19/00 (2011.01)
A61B 6/00 (2006.01)

(52) U.S. Cl.
CPC .......... *G06F 19/3437* (2013.01); *A61B 6/504* (2013.01); *A61B 6/507* (2013.01); *A61B 6/5217* (2013.01)

(58) Field of Classification Search
CPC ......... A61B 6/52; A61B 6/504; G06F 17/00; G06F 19/3437
See application file for complete search history.

(56) References Cited

U.S. PATENT DOCUMENTS

2011/0245656 A1* 10/2011 Bammer ......... G01R 33/56366
600/411

OTHER PUBLICATIONS

"A General Kinetic Model for Quantitative Perfusion Imaging with Arterial Spin Labeling" by R.B. Buxton et al. Magnetic resonance in medicine 40.3 (1998): p. 383-396.*

* cited by examiner

*Primary Examiner* — Tse Chen
*Assistant Examiner* — Jason Ip
(74) *Attorney, Agent, or Firm* — Thomas | Horstemeyer, LLP

(57) ABSTRACT

Systems and methods are disclosed for quantifying absolute blood volume flow rates by fitting a kinetic model incorporating blood volume, bolus dispersion and signal attenuation to dynamic angiographic data. A self-calibration method is described for both 2D and 3D data sets to convert the relative blood volume parameter into absolute units. The parameter values are then used to simulate the signal arising from a very short bolus, in the absence of signal attenuation, which can be readily encompassed within a vessel mask of interest. The volume flow rate can then be determined by calculating the blood volume within the vessel mask and dividing by the simulated bolus duration. This method is exemplified using non-contrast magnetic resonance imaging data from a flow phantom and the cerebral arteries of healthy volunteers and a patient with Moya-Moya disease acquired using a 2D vessel-encoded pseudo-continuous arterial spin labeling pulse sequence. This allows flow quantification in downstream vessels from each brain-feeding artery separately. The systems and methods can be of use in patients with a variety of cerebrovascular diseases, such as the assessment of collateral flow in patients with steno-occlusive disease or the evaluation of arteriovenous malformations.

14 Claims, 17 Drawing Sheets
(10 of 17 Drawing Sheet(s) Filed in Color)

QUANTIFICATION OF BLOOD VOLUME FLOW RATES FROM DYNAMIC ANGIOGRAPHY DATA

CROSS REFERENCE TO RELATED APPLICATIONS

This application claims priority to U.S. provisional application entitled "QUANTIFICATION OF BLOOD VOLUME FLOW RATES FROM DYNAMIC ANGIOGRAPHY DATA" having Ser. No. 61/685,598, filed Mar. 20, 2012, which is hereby incorporated by reference in its entirety.

INCORPORATION BY REFERENCE

Applicant incorporates by reference the following publications as if they were fully set forth herein expressly in their entireties:
1) Chappell, M. A., Okell, T. W., Jezzard, P., Woolrich, M. W., 2010. A general framework for the analysis of vessel encoded arterial spin labeling for vascular territory mapping. Magn Reson Med 64, 1529-39.
2) Chappell, M. A., Okell, T. W., Payne, S. J., Jezzard, P., Woolrich, M. W., 2012. A fast analysis method for non-invasive imaging of blood flow in individual cerebral arteries using vessel-encoded arterial spin labelling angiography. Medical Image Analysis 16, 831-839.
3) Chappell, M. A., Woolrich, M. W., Kazan, S., Jezzard, P., Payne, S. J., Macintosh, B. J., 2013. Modeling dispersion in arterial spin labeling: Validation using dynamic angiographic measurements. Magn Reson Med 69, 563-570.
4) Okell, T. W., Chappell, M. A., Schulz, U. G., Jezzard, P., 2012. A kinetic model for vessel-encoded dynamic angiography with arterial spin labeling. Magnetic Resonance in Medicine 68, 969-979.
5) Okell, T. W., Chappell, M. A., Woolrich, M. W., Günther, M., Feinberg, D. A., Jezzard, P., 2010. Vessel-encoded dynamic magnetic resonance angiography using arterial spin labeling. Magn Reson Med 64, 698-706.
6) Okell, T. W., Schmitt, P., Bi, X., Chappell, M. A., Tijssen, R. H., Miller, K. L., Jezzard, P., 2011. 4D vessel-encoded arterial spin labeling angiography, in: Proceedings 19$^{th}$ Scientific Meeting, ISMRM, Montreal, p. 4034.
7) Each and every one of the rest of the publications listed in the References section appended hereto.

TECHNICAL FIELD

The present disclosure generally relates to medical imaging and more particularly, relates to systems and methods for providing clinicians with quantitative blood volume flow rate information to help make diagnostic, prognostic or therapeutic decisions.

BACKGROUND

Angiographic methods, which generate images of blood vessels, are of great importance in the assessment of vascular diseases, such as atherosclerosis. They can provide information on vessel morphology and function which aids clinicians with diagnosis, prognosis and treatment planning in these patients. Vessel-selective angiography provides additional information about the relative importance of each feeding artery which can be useful in a number of areas, such as the assessment of collateral blood flow or the evaluation of blood supply to a tumor or arteriovenous malformation. However, many angiographic methods provide only qualitative information on blood flow, making objective comparisons between vessels and across subjects difficult. In addition, many of these methods have a number of other drawbacks such as the requirement for an invasive procedure, use of ionizing radiation or the administration of a contrast agent.

Phase-contrast magnetic resonance angiography (MRA) (e.g., Dumoulin and Hart, 1986) attempts to provide quantitative blood velocity and flow rate measurements, but it could not be easily combined with a vessel-encoded or vessel-selective preparation to give vessel-specific information about blood flow in downstream vessels. Further, it is hampered by long scan times (Miyazaki et al., 2008) and insensitivity to slow flowing blood. Previous methods for quantification of arterial spin labeling (ASL) dynamic angiography (van Osch et al. 2006) have been limited to pulsed ASL techniques which are less Signal-to-Noise Ratio (SNR) efficient than continuous or pseudo-continuous approaches, require additional calibration scans to be carried out, and make the assumption of plug flow through the vessels.

In addition to blood flow quantification, the ability to visualize blood flow in a vessel-selective manner is of importance in a range of cerebrovascular diseases. For example, in patients with steno-occlusive disease, this information reveals the extent of collateral blood flow, which is important for maintaining the viability of brain tissue when the primary feeding artery is compromised (Liebeskind, 2003). Clinically, such assessments are generally performed using x-ray digital subtraction angiography (DSA) which provides excellent temporal and spatial resolution, but is limited by its invasive nature, the use of ionizing radiation and the requirement for catheter repositioning to assess multiple arteries. In addition, these procedures carry a risk of contrast agent reaction, silent ischaemia (Bendszus et al., 1999), or even stroke (Kaufmann et al., 2007). Other angiographic methods, such as conventional time-of-flight (TOF) magnetic resonance angiography (Masaryk et al., 1989), lack hemodynamic and vessel-selective information.

Non-invasive vessel-selective perfusion mapping methods, such as those based on arterial spin labeling (ASL) (Hendrikse et al., 2004; Werner et al., 2005; Gunther, 2006; Wong, 2007; Dai et al., 2010; and Helle et al., 2010), can be quantitative, allow the inference of abnormal flow patterns and have been shown to correlate well with x-ray DSA for the assessment of collateral flow (Chng et al., 2008; and Wu et al., 2008). However, the vessel morphology and flow patterns are not visualized directly, and in patients with very delayed blood arrival T1 decay may lead to significant signal attenuation before the blood reaches the tissue.

Recently, we proposed a method for vessel-selective dynamic angiography (Okell et al., 2010) by combining a vessel-encoded pseudo-continuous arterial spin labeling (VEPCASL) preparation (Wong, 2007) with a 2D thick-slab flow-compensated segmented Fast Low Angle Shot (FLASH) readout (Gunther et al., 2002; and Sallustio et al., 2008). This technique requires no catheter insertion or contrast agent and provides useful qualitative information on the morphological and functional status of each artery. However, it is hampered by the lack of quantitative information. In particular, late arriving blood will appear less intense due to the greater T1 decay which may bias the observer's interpretation of the data. In addition, in order to optimize the signal-to-noise ratio (SNR) a long labeling duration is generally used, so the first acquired image corresponds to a time at which most of the vessels are filled with labeled blood and thus only outflow of the bolus can be observed.

It is therefore desirable to develop a system and method for quantification of blood volume flow rate in specific vessel segments using dynamic angiographic data that can also account for attenuation of the measured signal.

A simple modification of perfusion quantification methods (such as the general ASL kinetic model [Buxton et al., 2008]) are not appropriate since they assume accumulation of the contrast agent within each voxel, which does not occur in large vessels. Indeed, the signal strength measured in these experiments depends mainly on blood volume, not blood flow. It is the total volume of labeled blood created by labeling for a specific time which is crucial here. The attenuation of the signal amplitude must also be accounted for.

Accordingly, there is a need to address the aforementioned deficiencies and inadequacies.

SUMMARY

The systems and methods disclosed herein provide quantification of blood volume flow rates, avoiding the aforementioned disadvantages, For example, the present systems and methods provide a framework in which any dynamic angiography data, including arterial spin labeling (ASL) and x-ray angiographic data, can be quantified to give volume flow rates (ml/s) in each major artery along with arrival time and bolus dispersion information. A general kinetic model is incorporated to describe the signal in generic dynamic angiography acquisitions, accounting for bolus dispersion and signal attenuation. A specific example of this general model, which applies to VEPCASL dynamic angiography, is given by Okell et al. 2012 (Okell, T. W., Chappell, M. A., Schulz, U., and Jezzard, P. A. kinetic model for vessel-encoded dynamic angiography with arterial spin labeling. Magn Reson Med (2012), DOI: 10.1002/mrm.23311), which is incorporated by reference as if fully set forth herein. This model is also applicable to techniques based on continuous or pseudo-continuous ASL. In a similar fashion this general model can be extended to any other dynamic angiographic data.

In an aspect we provide systems and methods for absolute blood volume flow rate quantification using generic dynamic angiographic data. This may involve the fitting of a kinetic model in each voxel, accounting for relative blood volume, delayed blood arrival, bolus dispersion and signal attenuation. A self-calibration method may also be provided for relating the relative blood volume parameter to absolute blood volume in either 2D or 3D acquisitions, using the same data set. Using these results a method for quantifying blood volume flow rate by simulating a very short bolus of labeled blood is provided. Our systems and methods have the advantages of not requiring an invasive procedure, the administration of a contrast agent or exposure to ionizing radiation.

The parameter maps produced from the present systems and methods incorporating and resulting from fitting this model to the data in each voxel or subset of voxels provide information relating to blood volume, blood arrival time and bolus dispersion, which could provide useful indicators of disease in patient groups and guidance for those incorporating dispersion into models of tissue perfusion. These maps also allow the generation of synthesized blood flow images in the absence of signal attenuation with arbitrary temporal resolution (e.g. for visualizing blood inflow), giving an intuitive and unbiased representation of the data and, for example, improving the conspicuity of vessels with delayed arrival in acquisitions where the tracer decays with time (such as ASL). In vessel-selective acquisitions, the maps relating to blood volume can further be used to quantify the relative blood volume flow rates in downstream vessels from each of the feeding arteries, showing the importance of each feeding artery.

For blood volume flow rate quantification, in an embodiment, the present systems and methods consider that for a very short labeling duration, all the labeled blood is likely to be contained within a vessel segment of interest at one point in time. By estimating the total volume of labeled blood within this vessel segment, then with knowledge of the labeling duration, the volume flow rate can be calculated simply as the volume divided by the time. However, use of very short labeling durations leads to poor SNR and account must still be taken of signal attenuating effects. To avoid this problem, the present systems and methods fit the time evolution of the angiographic signal in each voxel to a kinetic model (as described above). Once the arrival time, blood volume and dispersion effects have been measured and a calibration procedure performed, very short bolus duration can be simulated in the absence of signal attenuating effects, allowing absolute blood volume flow rate quantification to be performed.

Briefly described, one embodiment, among others, is a system and method for quantification of blood volume flow rates within a vessel mask, including blood vessels of interest, in a subject from dynamic angiography data, comprising:

A. Acquiring dynamic angiographic data which covers the blood vessels of interest in a subject;

B. Fitting a kinetic model to the dynamic angiographic data in each voxel or a subset of voxels deemed to contain the major blood vessels to derive parameter maps relating to relative blood volume, blood arrival time and dispersion of a blood bolus;

C. Determining a calibration factor and using the calibration factor to convert relative blood volume in each voxel or subset of voxels to absolute blood volume;

D. Using the derived parameter maps to simulate over a number of time points the expected signal that would arise from a bolus of labeled blood with a short duration relative to dispersion of the bolus in the absence of signal decay;

E. Summing the simulated signal within the vessel mask of interest and converting the summed signal into an estimate of absolute blood volume within the vessel mask using the calibration factor at each simulated time point; and F. Determining an absolute blood volume flow rate within the vessel mask of interest from the blood volume of step E and the simulated bolus duration at each simulated time point.

In an aspect the dynamic angiographic data is acquired by providing a medical imaging device, positioning the subject in association with the medical imaging device, and using the medical imaging device to acquire the data. The dynamic angiographic data may be either 2D or 3D data.

The system and method may optionally include use of the parameter maps to simulate blood flow at any desired time points (e.g., during blood arrival) in the absence of signal decay/attenuation for unbiased data visualization. Also, for artery-specific data, the system and method may optionally include determination of the relative blood volume flow rates from each feeding artery in well-mixed vessel segments. The system and method may also be optionally enhanced by assessment of time points during which the simulated bolus data lies entirely within a vessel mask of interest to obtain more robust estimates of the blood volume flow rate. The absolute blood volume flow rate may be output to a user for diagnosis, prognosis, a therapeutic decision or for use in research, or for example displayed on a monitor or other display device or printed.

Other systems, methods, features, and advantages of the present disclosure for providing quantification of blood volume flow rates from dynamic angiography data will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views. These drawings exemplify the present disclosure using VEPCASL dynamic angiographic data and the corresponding kinetic model, although any type dynamic angiographic data could be used here.

DETAILED DESCRIPTION

Figure 1:
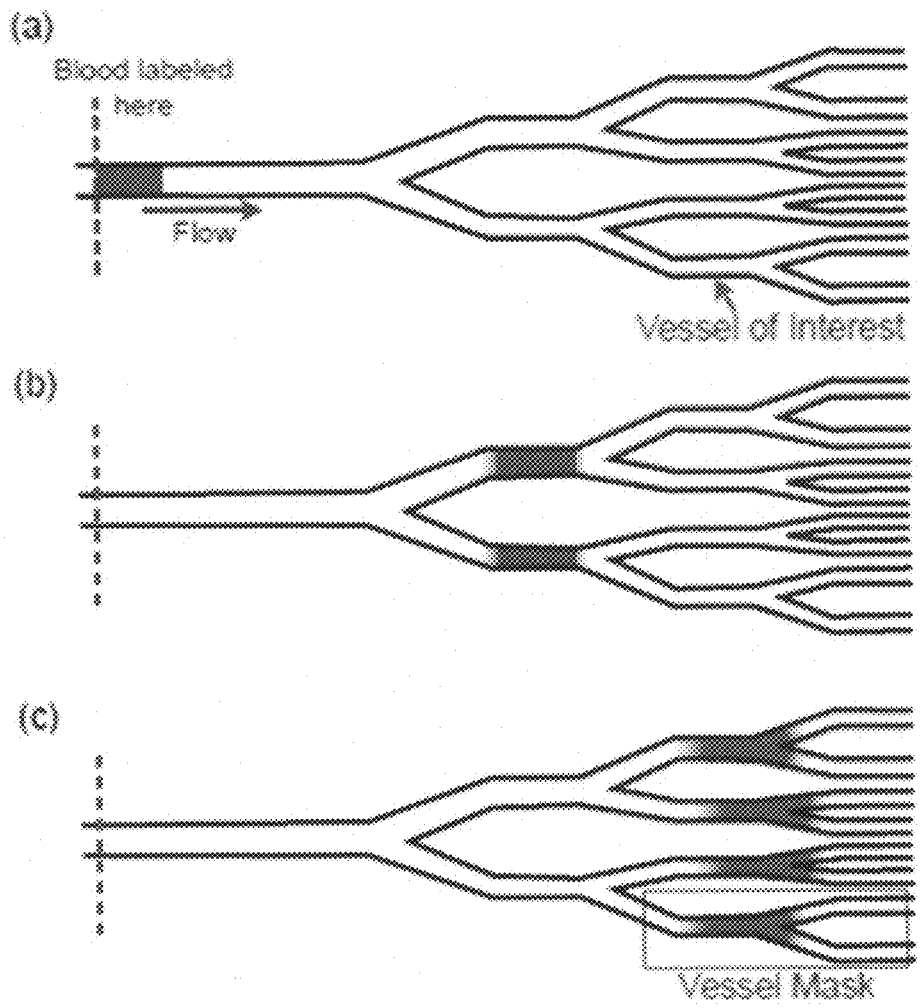
FIG. 1 is a schematic showing a general approach to flow rate quantification.

Having summarized various aspects of the present disclosure, reference will now be made in detail to the description of the disclosure as illustrated in the drawings. While the disclosure will be described in connection with these drawings, there is no intent to limit it to the embodiment or embodiments disclosed herein. On the contrary, the intent is to cover all alternatives, modifications and equivalents included within the spirit and scope of the disclosure as defined by the appended claims.

Systems and methods for quantification of blood volume flow rates from dynamic angiography data are now described. As an example, consider a dynamic angiography experiment (as illustrated in FIG. 1) using a rect-shaped uniform bolus blood of duration, $\tau$, where all of the blood flowing through a defined point in an upstream proximal vessel is perfectly labeled, as in FIG. 1a. Assuming that there is no flow pulsatility and that the subject's physiology remains constant, the volume of blood which is labeled must flow through the vessel network every time period $\tau$. By extension, the volume of this labeled blood which flows into any downstream vessel must also flow through that vessel during every time period $\tau$. Even if the bolus disperses during its passage, by the conservation of mass the volume of labeled blood flowing into the vessel will not be affected. Therefore, the blood volume flow rate within a downstream vessel can be calculated simply as the volume of labeled blood which flows into it divided by the bolus duration, $\tau$.

As depicted in FIG. 1(b) the bolus from a proximal vessel travels into the vessel network, splitting according to the flow ratios between different branches, and begins to disperse: In FIG. 1(c) the bolus arrives in the vessel of interest. If the spatial extent of the bolus, including dispersion, is small enough to be encompassed within a mask drawn over the vessel of interest and any downstream branches, then the volume of labeled blood which has flowed into this vessel can be estimated. This volume of blood is generated during time $\tau$, and must therefore flow into the vessel of interest during every time period, $\tau$, if the flow rate is constant. The blood volume flow rate into the vessel of interest can therefore be calculated by taking the volume of labeled blood within the vessel mask and dividing by $\tau$.

In order to be able to accurately estimate the volume of labeled blood which ends up in a vessel of interest, the entire bolus of labeled blood must be present in that vessel, or its downstream branches, at one point in time. To achieve this, a very short bolus duration can be used to ensure that the spatial extent of the bolus is small. This may be sufficient to ensure that the entire bolus is present in the vessel of interest at one point in time, even in the presence of dispersion, and the total volume of labeled blood within this vessel can be estimated from the measured signal intensity. This can be sufficient to estimate the blood volume flow rate within that vessel. However, to perform such an experiment would be difficult: in some angiographic modalities a rect-shaped bolus with uniform labeling cannot be achieved, the use of a short labeling duration leads to poor SNR (Okell et al., 2010) and decay of the signal during imaging would further confound the measurement.

To overcome these problems (for example poor signal-to-noise ratio (SNR) and signal decay), we use a kinetic model which describes the time evolution of the signal in a single voxel or subset of voxels from a given feeding artery, incorporating blood volume, arrival time, bolus dispersion and signal attenuation, for example, due to $T_1$ decay and effects from the imaging RF pulses. This model is a description of how we expect the signal will vary over the time duration of a bolus within a single voxel. This model can be fitted to high SNR data acquired using a long labeling duration. Once the model parameters in each voxel have been estimated, a theoretical signal arising from a more ideal very short bolus experiment can be simulated over an arbitrary range of time points in the absence of $T_1$ decay and radio frequency (RF) effects. By a very short bolus we mean a blood bolus whose duration is small compared to the time scale of the dispersion of the bolus. In an embodiment this can be approximately one millisecond or less. After signal calibration the blood volume within a vessel of interest can be calculated, and thus the blood volume flow rate can be determined.

Figure 2:
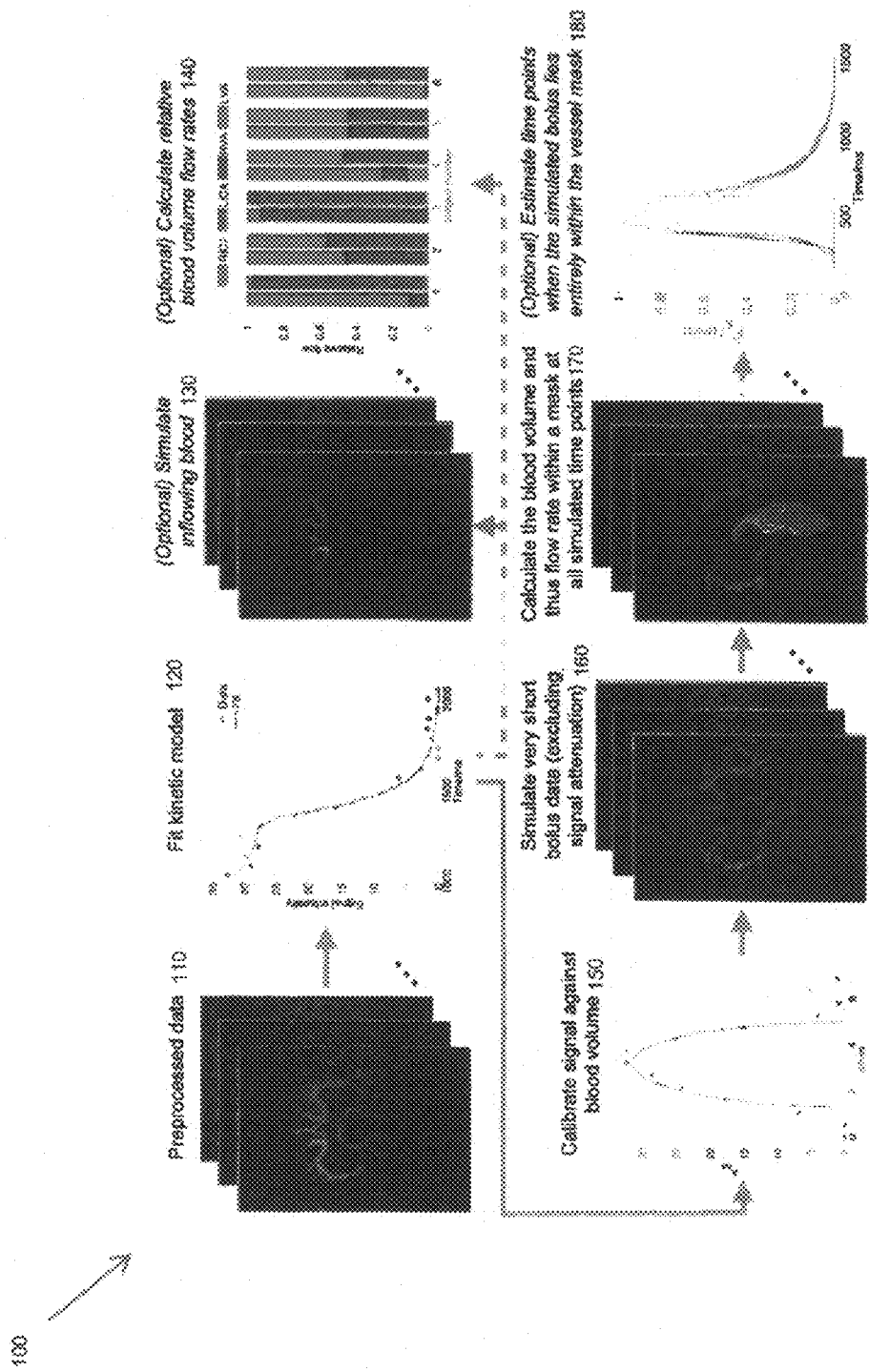
FIG. 2 depicts the processing stages for one embodiment of the present systems and methods for quantifying blood volume rates from dynamic angiography data.

FIG. 2 outlines the processing stages for one embodiment of our present systems and methods for quantification of blood volume flow rates from dynamic angiography data. We first acquire dynamic angiographic data which covers the blood vessels of interest in a subject. The data may be acquired, for example, by providing a medical imaging device and positioning a patient in proximity to the device. Images, or data, can be acquired. In the case of a magnetic resonance imaging (MRI) device this can be from a combination of images from separate coils of the device, for example dynamic angiographic data.

This data may then go through a pre-processing stage 110 where the data may be corrected, for example, for spatial non-uniformity in the images, separation of the signal from multiple feeding arteries, etc. Parameter maps can be derived relating to, for example, relative blood volume within vessels of interest, blood arrival time and bolus dispersion by fitting a kinetic model to the acquired data 120. The parameter maps may optionally be used to simulate 130 blood flow at any desired time points (e.g. inflowing blood) in the absence of signal decay/attenuation for unbiased data visualization. Additionally, for artery-specific data, calculation of the relative blood volume flow rates from each feeding artery in well-mixed vessel segments may be carried out 140.

A calibration factor can be determined and used to convert the relative blood volume parameter in each voxel or subset of voxels into absolute blood volume 150. In the case of 3D data with sufficient spatial resolution to ensure there are one or more voxels that lie entirely within a blood vessel, this calibration factor can be readily determined from the same data set. For 2D data the volume of blood leading to the measured signal is unknown. One possible calibration method is one that assumes circular vessel cross-sections, allowing the calibration factor to be derived from the same data set.

Very short labeling duration data is then simulated 160 in the absence of signal decay/attenuation. This simulation results in the generation of data or images of blood flow without bias from, for example, $T_1$ decay and radio frequency (RF) effects. Such a simulation depicts what the data would look like if the prior steps were performed for a very short period of time relative to the time scale for the dispersion of the blood bolus. The shorter the period of time for the simulation the better chance of capturing the entire dispersed bolus within a vessel mask of interest.

Next, a determination of the blood volume and thus blood flow rate within a vessel mask at all simulated time points can be made 170. An absolute blood volume flow rate can be determined using the calibration factor and summing the signals within a vessel mask of interest at each simulated time point. In one embodiment, to measure blood volume flow rate accurately the entire blood bolus should be within the vessel mask of interest. Optionally, an assessment or estimate of time points during which the simulated blood bolus lies entirely within the vessel mask can be made to obtain a more robust assessment of the blood volume flow rate, for example by averaging the estimated flow rate over these time points. Alternatively, the estimated blood volume flow rate could be reported at a single time point chosen manually.

General Kinetic Model

In many types of dynamic angiographic data, the relative concentration of labeled blood (be it from a spin labeling type method or an exogenous contrast agent) in proximal vessels is known or can be measured, and the decay/attenuation of this label over time can be described mathematically. Using this information a kinetic model describing the signal variation, S, in a single voxel, i, at position r, over time, t, can be generally described as:

$$S(r_i,t) = A(r_i) \int_{-\infty}^{\infty} dt_d c_{in}(t-t_d-\delta_t) D(r_i,t_d) T(\delta_t,t_d,t) R(\delta_t,t_d,t),$$ [Eqn 1]

wherein A is proportional to the blood volume within the voxel, $v(r_i)$, such that $A(r_i)=S_0 v(r_i)$, where $S_0$ is the calibration factor relating blood volume to measured signal in the absence of signal attenuation, $t_d$ is the time by which blood is delayed due to dispersion, $c_{in}$ is the relative concentration of the tracer in a proximal vessel, $\delta_t$ is the time taken by the blood to travel from this proximal vessel to the voxel, D is a normalized dispersion kernel describing the fraction of blood delayed by time $t_d$ due to bolus dispersion, T is a general function for decay of the tracer over time and R is a general function describing attenuation of the signal by the imaging method.

This equation assumes the measured signal is proportional to the volume of the tracer within each voxel. For imaging modalities where this is not the case an appropriate conversion would have to be performed either as a preprocessing step or incorporated into the kinetic model. Note that this model can be used to fit data from multiple feeding arteries whose signals have been separated in preprocessing. The fit to the signal from artery j gives $A_j(r_i)=S_0 v(r_i)$ wherein $v_j$ is the volume of blood within the voxel originating from artery j.

Example Kinetic Model for Continuous or Pseudo-Continuous ASL

In the case of continuous or pseudo-continuous arterial spin labeling (CASL or PCASL, including VEPCASL) the derivation of the kinetic model used herein to describe the signal evolution in a single voxel from a given feeding artery has been previously reported (Okell et al., 2012). The present system and methods employ this novel kinetic model described in more detail below, incorporating effects due to $T_1$ decay, imaging RF pulses and dispersion of the labeled blood as it passes through the vasculature.

This signal, S, measured in a single voxel at time t will depend upon the relative concentration of the tracer in a proximal vessel, $c_{in}$. This tracer takes a time $\Delta t$ to arrive at the voxel. An additional delay, t', due to dispersion is modeled by convolution with a dispersion '). For clarity, the variables used in this paper are listed in Table 1.

Signal attenuation due to tracer decay and resulting from the imaging method are described by multiplicative factors T and $\Psi$ respectively. The measured signal is also scaled by the volume of blood within the voxel, v, and a calibration factor, $S_0$, which relates blood volume to measured signal in the absence of signal attenuation, which we combine into a single scaling factor $A=S_0 v$.

Note that in this type of acquisition, $S_0$ accounts for the equilibrium magnetization of blood, the excitation flip angle used, the inversion efficiency of the ASL labeling and the sensitivity of the coil. It is assumed in this discussion that the data have been corrected for non-uniform coil sensitivity profiles in pre-processing, so that $S_0$ is constant across the image.

In this particular case the general functions described above take the following forms:

$$c_{in}(t) = \begin{cases} 0 & t < 0 \\ 1 & 0 \le t < \tau \\ 0 & t \ge \tau \end{cases}$$ [Eqn 2]

where $\tau$ is the labeling duration and t=0 corresponds to the start of the labeling.

Note that although the relative concentration of labeled water takes a value of one here, this does not imply that the labeling efficiency is 100%. A reduced labeling efficiency would result in a global reduction of the measured signal, which is incorporated into the calibration factor, $S_0$.

For the VEPCASL data used in our study we chose a gamma variate model for D characterized by sharpness, s, and time to peak, p. In this case T represents decay of the label due to $T_1$ relaxation and $\Psi$ represents signal attenuation due to the imaging radio frequency (RF) pulses. Note that $\Psi$ depends on the time at which blood first arrives in the imaging region, $\Delta t_{min}$, which is determined as an explicit step in preprocessing (described below) rather than being fitted from the data. This leaves four free parameters in each voxel: A, $\Delta t$, s and p. The explicit mathematical forms for D, T and $\Psi$ relevant for VEPCASL angiography can be found in our previous paper (Okell et al., 2012).

For clarity we define $c_{ideal}$ as the "ideal" relative concentration of labeled blood passing through a point in space, r, in the absence of bolus dispersion and signal attenuation:

$$c_{ideal}(r, t) = \kappa(r) c_{in}(t - \delta_t(r)) = \begin{cases} 1 & t < \delta_t \\ \kappa(r) & \delta_t \le t < \delta_t + \tau \\ 0 & t \ge \delta_t + \tau \end{cases}$$ [Eqn 3]

where $\kappa(r)=1$ inside an artery and is zero elsewhere. $c_{ideal}$ is plotted in FIG. 3a along with other factors that affect the final model.

In an embodiment, we choose a gamma variate function for the dispersion kernel, D, (FIG. 3b) which has been used previously to model the inflow of an injected bolus of contrast agent (Rausch et al., 2000) or pulsed ASL preparation (Macintosh et al., 2011). Here we consider the bolus dispersion rather than the entire bolus time-course. This function has the desirable properties of being causal and the ability to model a long tail, suitable for describing blood flowing in a laminar fashion. We use a parameterization similar to that described by Rausch et al. (2000):

$$D(r, t_d) = \begin{cases} \dfrac{s}{\Gamma(1+ps)} e^{-s t_d} (s t_d)^{ps} & s t_d > 0, ps > -1 \\ 0 & \text{otherwise} \end{cases}$$ [Eqn 4]

where p(r) describes the time to peak of the distribution, s(r) is the sharpness of the distribution (a low sharpness implies a distribution with a long tail) and Γ is the gamma function which normalizes the kernel to unit area:

$$\Gamma(1+ps) = \int_0^\infty dt_d s e^{-st_d}(st_d)^{ps} \quad \text{[Eqn 5]}$$

Figure 3:
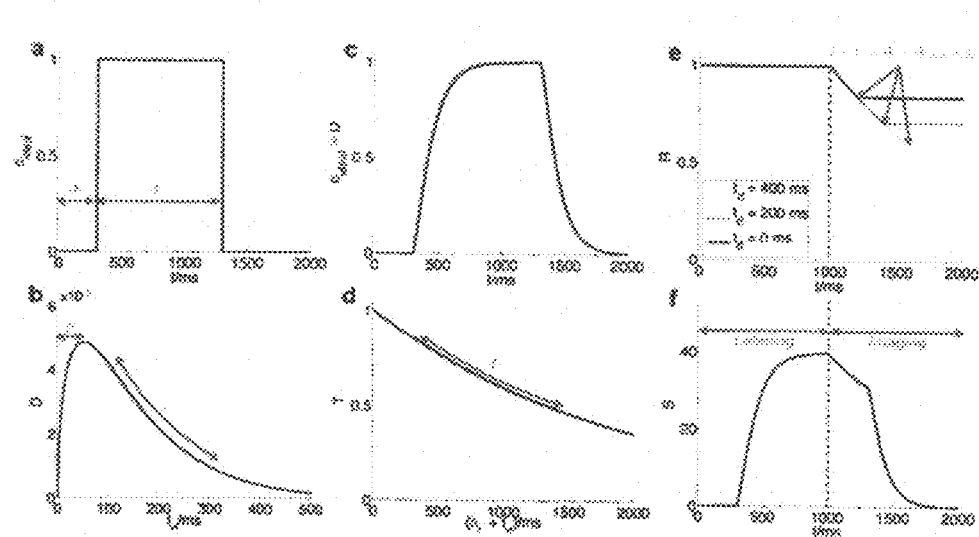
FIG. 3 Illustrates various factors which contribute to one embodiment of a kinetic model of the present disclosure describing the signal evolution in a single voxel: wherein, the ideal labeled blood concentration is a rect function (a); convolution with a dispersion kernel (b) yields a modified curve (c); account must also be taken of $T_1$ decay (d) and effects due to the Radio Frequency (RF) excitation pulses (e, plotted for three different time values during which blood is delayed due to dispersion, $t_d$). Combining these effects yields the final curve (f) which is scaled by calibration factor, $S_0$, and blood volume.

The convolution of $c_{ideal}$ with the gamma variate dispersion kernel is shown in FIG. 3c.

$T(\delta_t, t_d)$ describes the $T_1$ decay experienced by the blood after labeling during its transit to the observation point (FIG. 3d). After labeling it takes the blood a time $\delta_t + t_d$ to reach the position of interest, so:

$$T(\delta_t, t_d) = \exp(-(\delta_t + t_d)/T_{1b}) \quad \text{[Eqn 6]}$$

where $T_{1b}$ is the longitudinal relaxation time of arterial blood, which is assumed to be equal to 1664 ms (Lu et al., 2004) for experiments at 3 Tesla.

$R(t, \delta_t, t_d)$ describes the attenuation of the ASL signal by the excitation RF pulses as the blood passes through the imaged region (FIG. 3e). Assuming all transverse magnetization is effectively spoiled at the end of every repetition time (TR) period, each RF pulse with flip angle α reduces the longitudinal magnetization by a factor of cos α. This applies to both the inverted and non-inverted blood and therefore the ASL signal is attenuated by the same factor.

$$R(t, \delta_t) = (\cos \alpha)^{N(r,t,t_d)} \quad \text{[Eqn 7]}$$

where $N(r, t, t_d)$ is the previous number of RF excitation pulses experienced by the blood at position r, time t and time delay $t_d$. In the simplest case that the imaging region encompasses everything distal to the labeling plane, then all the labeled blood has experienced all the previous RF pulses so N can be written using a simple expression:

$$N(r, t, t_d) = N(t) \approx \frac{t - t_o}{T_R} \quad \text{[Eqn 8]}$$

where $t_0$ is the time at which the first imaging pulse is played out and we make a continuous approximation for N for simplicity, in a similar manner to Günther et al., 2001. However, it is often the case for transverse acquisitions that there is a gap between the labeling plane and the imaging region within which blood does not experience the imaging pulses. This problem is similar to that faced by standard ASL acquisitions using a Look-Locker readout (Günther et al., 2001; Petersen et al., 2006). However, here we consider RF effects before the blood reaches the voxel of interest and we also account for differences across the dispersed bolus.

If the blood from a given feeding artery takes a time $\delta_{t,min}$ to reach the imaging plane then the maximum amount of time spent in the imaging region before reaching the voxel of interest is $\delta_t - \delta_{t,min} + t_d$. This equation assumes that the bolus is relatively undispersed upon entry to the imaging region in order to simplify the expression. This maximum time spent in the imaging region limits the number of RF pulses experienced by the blood, so the expression for N becomes:

$$N(r, t, t_d) \approx \min\left\{\frac{t - t_o}{T_R}, \frac{\delta_t - \delta_{t,min} + t_d}{T_R}\right\} \quad \text{[Eqn 9]}$$

Note that RF effects are not present before the start of imaging and the curve (FIG. 3e) flattens out to a constant when the time relative to the start of imaging is greater than the time the blood has spent in the imaging region (which varies with $t_d$).

If we assume that $\delta_t$, s and p are approximately constant over the dimensions of the voxel (including across the imaging slab in 2D acquisitions) then we arrive at our final model (FIG. 3f):

$$S(r_i, t) = A(r_i) \int_{t-\delta_t} \tau^{-\delta_t} dt_d D(r_i, t_d) T(\delta_t, t_d) R(t, \delta_t, t_d) \quad \text{[Eqn 10]}$$

Assuming that the earliest arrival of blood in the imaging region, $\delta_{t,min}$, is known (see Methods section below), this model takes four parameters: A, $\delta_t$, s and p.

Note that for long labeling durations ($\tau > \delta_t$) only the latter portion of the curve will be observed (as shown in FIG. 3f) since imaging cannot commence until the labeling has finished. Parameters used for the plots in FIG. 2 are: A=50, $\delta_t$=300 ms, s=0.01 ms$^{-1}$, p=50 ms, $\delta_{tmin}$=100 ms.

Calibration

The kinetic model described above allows only relative blood volume to be determined, and hence only relative blood volume flow rate. In order to determine absolute blood volume flow rates, a calibration factor $S_0$ must be determined. If a 3D angiography acquisition were performed and one or more voxels small enough to fit entirely within an artery could be found then this should be sufficient for the calibration. Fitting, for example Eqn 1 to such voxels can yield an estimate of A for each feeding artery, the sum of which we define as $A_{tot}$. Since the sum of $v(r_i)$ over all feeding arteries must be equal to the voxel volume $\Delta x \Delta y \Delta z$ we can write:

$$\hat{S}_0 \approx \left\langle \frac{A_{tot}}{\Delta x \Delta y \Delta z} \right\rangle_{vessels\ within\ arteries} \quad \text{[Eqn 11]}$$

Figure 4:
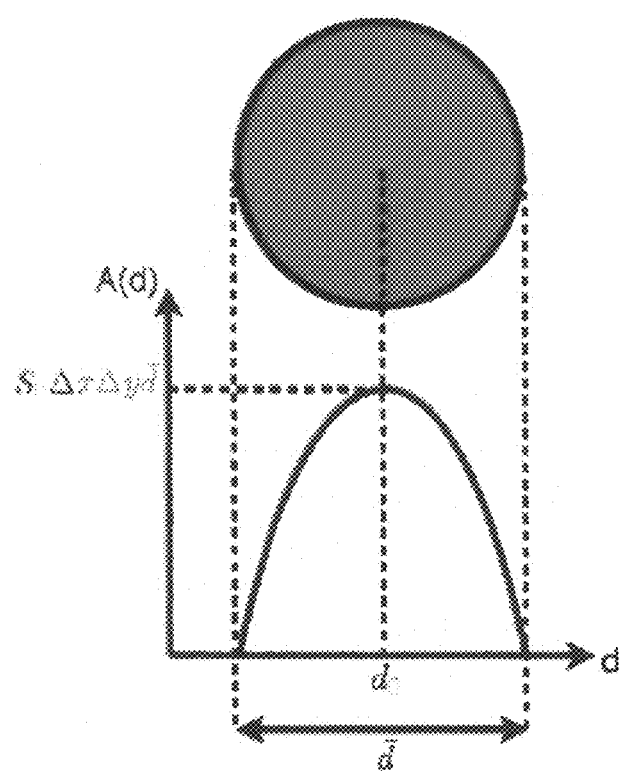
FIG. 4 depicts vessel geometry used to estimate an exemplary calibration factor, $S_0$, using two-dimensional dynamic angiographic data.

In a 2D acquisition, where a thick slab is imaged to yield a 2D projection of the vascular network, the volume of blood leading to the measured signal is unknown. However, if the vessel can be identified that runs parallel to the imaging plane and it is assumed that the cross section of each vessel is approximately circular, then measurements of vessel diameter, $\bar{d}$, within the imaging plane can be used to estimate the volume of blood producing the measured signal and therefore $S_0$. Plotting a profile of $A_{tot}$ against distance, d, perpendicular to the vessel direction (see FIG. 4) allows a fit to both $\bar{d}$ and $S_0$ simultaneously by considering the equation for a circle, to give:

$$A_{tot}(d) = \begin{cases} S_0 \Delta x \Delta y \sqrt{\bar{d}^2 - 4(d - d_0)^2} & |d - d_0| \leq \bar{d}/2 \\ 0 & |d - d_0| > \bar{d}/2 \end{cases} \quad \text{[Eqn 12]}$$

where $d_0$ is the location of the centre of the vessel, and $\Delta x$ and $\Delta y$ are the voxel dimensions.

Flow Rate Quantification within a Vessel Segment

The volume flow rate of blood, $F_g$, in a given vessel, g, is given by the volume of blood passing through it per unit period of time. As discussed above, under constant flow rate conditions, the volume of labeled blood which flows into this vessel, $V_g$, arises from labeling for a time $\tau$, and thus must flow into this vessel during every time interval, $\tau$. Therefore the volume flow rate can be written as:

$$F_g = \frac{V_g(\tau)}{\tau} \quad \text{[Eqn 13]}$$

As mentioned previously, in order to get an accurate estimate of $V_g$, the labeled bolus must be entirely contained within vessel g and the imaging region. In addition, signal attenuating effects must not be present. This can be achieved by using the parameter estimates derived from fitting the kinetic model described above to the data to simulate the signal, S', which would arise from a very short labeling duration, r', during which $c_{in}=1$, in the absence of signal attenuation (i.e. T=R=1):

$$S'(r_i,t) = A(r_i) \int_{t-\delta_i-\tau'}^{t-\delta_i} dt_d(r_i,t_d) \quad \text{[Eqn 14]}$$

Summing this simulated signal across a mask encompassing vessel g (which may include its downstream branches) and dividing by the calibration factor $S_0$ gives an estimate of the labeled blood volume within the vessel at the specified time. For times during which the simulated bolus lies entirely within the mask and imaging region, the volume flow rate can be estimated as:

$$\hat{F}_g = \frac{1}{\tau'} \sum_{i \in g} \frac{s'(r_i, t)}{S_0} \quad \text{[Eqn 15]}$$

Figure 5:
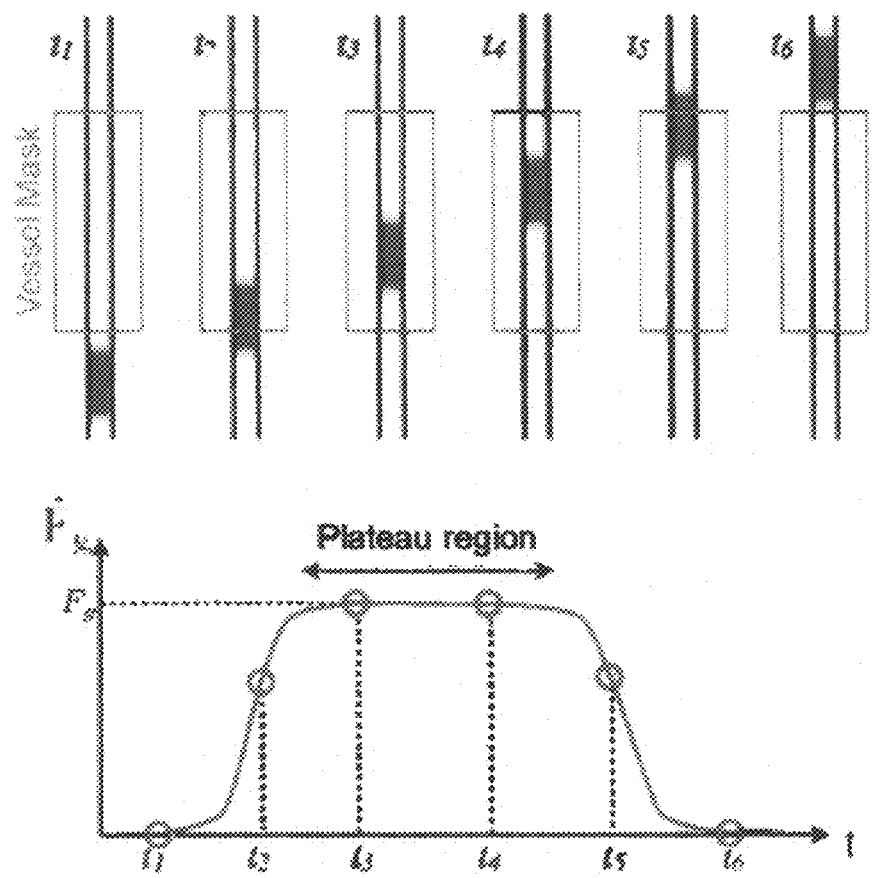
FIG. 5 is a schematic depiction of the expected variation in estimated blood volume flow rate, $\ddot{F}_g$, within a vessel mask as a function of simulated time.

$F_g$ should be independent of the time at which it is measured. Therefore, for any t where the labeled bolus is within the vessel mask and has not moved out of the imaging slab or started exchanging with tissue, the same volume flow rate can be calculated. Calculating $\hat{F}_g$ at multiple time points thus provides an opportunity to test the model and obtain a more robust estimate. FIG. 5 shows schematically the expected variation in the estimated blood volume flow rate within a vessel mask over a range of simulated time points.

It is noted that in cases where dispersion is very significant or where the vessel segment of interest is small, the simulated bolus may not lie entirely within the vessel mask and imaging slab at any of the simulated time points. In such a case the volume flow rate will be underestimated.

Methods

In order to demonstrate the flow rate quantification method described above we include here results from a study undertaken using the VEPCASL dynamic angiography method (Okell et al., 2010). All experiments were performed using a 3 Tesla Siemens MRI scanner (both TIM Verio and TIM Trio, Siemens Healthcare, Erlangen, Germany) using a 12 channel head coil for signal reception and body coil for transmission.

Flow Phantom Validation

A flow phantom was used to validate the present systems and methods by allowing comparison between known volume flow rates and those estimated using the method described above. The phantom consisted of a variable speed water pump (Ismatec SA, Zurich) connected to a long rubber tube with an internal diameter of approximately 4 mm. Two sections of this tube were secured to a foam pad inside the scanner bore with water running in opposite directions in the two sections. This foam pad was placed within the head coil along with a water bottle phantom to ensure appropriate coil loading.

A 3D time-of-flight (TOF) sequence was used for phantom localization and planning of the vessel-encoded scans. An additional TOF scan was acquired using the body coil for signal reception to allow correction for the variation in the head coil sensitivity across the field of view. 2D time-resolved VEPCASL angiography data were acquired as described by Okell et al. (2010) (voxel size 1.1×1.1 mm interpolated to 0.55×0.55 mm, slab thickness 50 mm, temporal resolution 55 ms, 20 time frames) with the exception that only four encoding cycles were necessary to separate the signal from the two tubes: non-selective tag, non-selective control, tag right tube whilst controlling left and tag left tube whilst controlling right. Acquisitions were performed over a range of flow phantom velocities. The true volume flow rate was measured during each acquisition by recording the time taken for the outlet tube to fill a measuring beaker to a fixed volume. This was repeated three times and the fixed volume divided by the average time taken to give the volume flow rate in ml/s.

Subjects and Scan Protocol

Six healthy volunteers with no known neurological disease were recruited (4 men, 2 women; age range, 24-39; mean age 32) under a technical development protocol agreed with local ethics and institutional committees. One patient with Moya-Moya disease (male, age 41) was also recruited under a protocol agreed with these committees. The scan protocol consisted of a 3D time-of-flight (TOF) sequence used to plan the vessel-encoded acquisitions followed by six-cycle 2D vessel-encoded dynamic angiography acquisitions (as per Okell et al., 2010) in transverse (50 mm imaging slab) and coronal (100 mm imaging slab) views centered on the circle of Willis. A sagittal acquisition was not performed due to the significant overlap of vessels in this view. The resulting images have an in-plane spatial resolution of 1.1×1.1 mm interpolated to 0.54×0.54 mm, and a temporal resolution of 55 ms. The scan time for the whole protocol was approximately 25 minutes. These data have been used in previous publications (Okell et al., 2010, 2012).

Data Preprocessing

Preprocessing was performed as per Okell et al. (2012). Complex images from each coil were combined using the adaptive combine method of Walsh et al. (Walsh et al., 2000), as described in our previous paper (Okell et al., 2010). The vascular components present in the resulting combined complex vessel-encoded data were separated using a maximum a posteriori (MAP) Bayesian solution (Chappell et al., 2012; method BT3) to the general framework for vessel-encoded analysis (Chappell, 2010), phase correction to convert the complex signals to real signals, correction for coil non-uniformity, determination of earliest blood arrival in the imaging region ($\Delta t_{min}$) and fitting of the kinetic model in high signal voxels for each feeding artery using a Bayesian framework.

The signal was separated into contributions from the four main brain feeding arteries: the right and left internal carotid arteries (RICA and LICA) and vertebral arteries (RVA and LVA). The analysis method used allows for rigid body translation and rotation of the arteries between the TOF and vessel-encoded acquisitions, thus attempting to account for the possibility of subject motion between the TOF scan and the subsequent VEPCASL acquisition. Laminar flow with average speed 30 cm/s was assumed in these large feeding arteries to reduce the computational complexity.

The output of the MAP processing is a complex signal value in each voxel at each time point for each vascular component. However, the model described above assumes purely real data. Simply taking the magnitude of the signal could skew the model fit, particularly when the signal is low and noise dominates, since the signal will then always be positive. To overcome this problem a voxel wise phase correction step was performed: the mean phase over time for each vascular component was calculated after weighting by the magnitude of the signal, since the phase of a low magnitude signal is less reliable. This mean phase was subtracted from the phase at each time point before taking the real part of the signal. It is assumed that the phase of the blood signal does not vary significantly over time and any phase variation is due to noise alone. This should be a reasonable assumption since each time frame is acquired 55 ms after the previous frame so the phase variation due to external sources such as $B_0$ drift should be minimal. This was confirmed by comparisons of phase corrected and magnitude images which show negligible differences when not close to the noise level.

The data were corrected for spatial non-uniformity in the coil transmission and reception fields, without the need for additional calibration scans, by using FMRIB's Automated Segmentation Tool (FAST) (Zhang et al., 2001) on the 3D TOF data. The resulting estimated bias field was transformed into the space of the vessel-encoded data using FMRIB's Linear Image Registration Tool (FLIRT) (Jenkinson et al, 2002) (using the known image coordinates, without a search) before being applied.

The kinetic model for VEPCASL dynamic angiography requires knowledge of the earliest time of arrival of blood in the imaging region ($\delta_{t,min}$) from each feeding artery in order to accurately describe the expected signal attenuation due to the imaging RF pulses. In the coronal view the labeling plane was encompassed within the imaging slab and therefore $\delta_{t,min}=0$ for all feeding arteries. However, for the transverse data sets $\delta_{t,min}$ was unknown and therefore had to be estimated before performing the full fit to the data. This was achieved separately for each feeding artery by fitting the kinetic model to a very restrictive mask containing only the highest intensity voxels corresponding to the large arteries just proximal to the circle of Willis. The mask was created by calculating the mean signal intensity over time for each vascular component and retaining only the 0.1% most intense voxels. For the purposes of this preliminary fitting procedure, $\delta_{t,min}$ was assumed to be zero, giving an imperfect fit to the data, but allowing reasonably accurate estimation of $\delta_t$.

Once these initial estimates of $\delta_t$ in the large proximal arteries had been made, the earliest arrival time in the imaging slab could be estimated for each feeding artery separately. One could take the minimum of these $\delta_t$ values, but this is potentially biased by noisy data, so instead the tenth percentile of these values was taken. In initial experiments this process was found to yield values which produced accurate fits to the full kinetic model.

The fitting of the kinetic model (Eqn. 10) was performed within a Bayesian framework. This allowed priors to be placed on the parameter values, helping to constrain them to reasonable values in the presence of noisy data. Assuming Gaussian noise on the data and Gaussian priors on each parameter the posterior probability of the parameters, given the data, can be calculated. Maximizing this posterior probability corresponds to finding the most likely set of parameters (i.e., the best fit to the data) and the curvature of this function at its maximum relates to the uncertainty on the parameters. This process was performed using a constrained optimization algorithm (fmincon) within Matlab® (Mathworks™, Natick, Mass., USA). Further details of the fitting procedure can be found in the appendix.

Fitting the kinetic model in voxels which do not contain vessels adds significantly to the computational time. Therefore in one embodiment the fitting procedure was only performed within a "high signal" mask which was found by calculating the mean signal intensity over time in each voxel, determining the 99th percentile of this value across the whole image (and all vascular components) and then excluding voxels which have mean signal of less than 40% of this value, which are assumed to be non-vascular voxels of no interest.

The generation of this high signal mask was modified slightly for data in the coronal view (including for the flow phantom) since it was noted that in very proximal vessels the blood washes out very rapidly, leading to a low mean signal and therefore exclusion from the mask. To overcome this limitation another mask was created in the same manner using the maximum, rather than the mean, signal over time, and the intersection of these two masks was used for the fitting.

Preprocessing of the flow phantom and healthy volunteer data differed slightly: for the flow phantom, the signal was separated into contributions from water originating from the two tubes plus static water. In healthy volunteers, the signal was separated into contributions from static tissue plus the four main brain feeding arteries: namely the right and left internal carotid arteries (RICA and LICA) and vertebral arteries (RVA and LVA). In addition, correction for coil non-uniformities in the flow phantom data was performed by using a body coil image as a reference, since the segmentation approach described above is not appropriate for such a phantom.

Optional Inflow Visualization

For inflow visualization the parameter estimates from the kinetic model were used to simulate the expected signal at a range of times during blood inflow in the absence of $T_1$ decay and RF effects (i.e. $T_{1b} \to \infty$ and $\alpha \to 0$). An infinite labeling duration was simulated to achieve inflow visualization in a similar fashion to x-ray DSA.

Optional Relative Volume Flow Rate Quantification

In healthy volunteers it is uncommon to expect blood from the major feeding arteries to provide a mixed supply to vessels above the circle of Willis, except in the posterior cerebral arteries (PCAs), so manual masks were drawn over the left and right PCA (P2 segments). The sum of A within each mask for each feeding artery was calculated and used to determine the relative flow rates, as described previously.

Calibration

Since the experimental data collected in this study consisted of 2D projections from thick slabs it was necessary to determine the blood calibration factor using the 2D method described above. Once the kinetic model fitting was complete a map of the parameter A, which is proportional to blood volume, was used to calibrate the signal. First, A was summed across all vascular components to give $A_{tot}$, which is proportional to the total blood volume within each voxel. The calibration factor, $S_0$, was then determined by fitting Eqn. 12 to a profile of $A_{tot}$ through ten vessel segments. The TOF images were used to ensure that the chosen vessel segments were running approximately parallel to the imaging plane. $S_0$ was then taken as the average of these measurements. In the transverse acquisitions this corresponded to three profiles through both left and right proximal middle cerebral arteries (M1 segments) and two profiles through both left and right proximal posterior cerebral arteries (P2 segments). In coronal acquisitions, four profiles were drawn through both left and right internal carotid arteries (two through the C1 segments and two through the C3 segments, as defined by Bouthillier et al. (1996)) and two through the distal basilar artery. To account for uncertainty in $S_0$ the standard error of its mean value was calculated. This uncertainty was propagated through to the flow rate quantification stage.

Flow Rate Quantification

Volume flow rate quantification was performed by simulating the signal, S', from a very short bolus duration (τ'=1 ms) in the absence of $T_1$ decay and RF effects (using Eqn. 14). Note that the choice of τ' should not have a significant impact on the flow rate quantification if it is small relative to dispersion of the bolus (i.e. p and 1/s). In our experiments in the cerebral vessels 1/s is on the order of 100 ms. To ensure that the measured volume flow rates were not dependent on the choice of τ', the processing of the flow phantom data was performed at a range of τ' values.

In order to propagate uncertainties in the fitting procedure through to the flow rate quantification a numerical estimate of the covariance matrix associated with the parameters was recorded as part of the fitting procedure (Okell et al., 2012). The parameter covariance matrix was used to determine a grid of points in parameter space over which the mean and variance of the simulated signal, S', were calculated, weighted by the true posterior probability of the parameters given the data.

As shown in FIG. 5 the estimated volume flow rate within a given vessel mask is expected to plateau during the time that the bolus is entirely within the mask. The top row shows a simulated bolus at a number of time points flowing through a vessel over which a mask has been drawn. At each time point the labeled blood volume within the mask is calculated and divided by the simulated bolus duration, τ', to give estimated blood volume flow rate, $\ddot{F}_g$. While the simulated bolus lies completely within the vessel mask ($t=t_3, t_4$), $\ddot{F}_g$ levels out to a constant value (the "plateau" region) equal to the true flow rate, $F_g$.

In an embodiment, to estimate this plateau region the approximate start and end times of the bolus passage through the mask were determined by thresholding the estimated volume flow rate at 20% of its maximum. Assuming the plateau occupies a significant proportion of this broad peak, the median value within it should be approximately equal to the volume flow rate within the plateau region and should also be relatively insensitive to noisy peaks and troughs in the curve. The plateau region was defined as the interval bounded by the times at which the estimated volume flow rate first and last exceeds this median value. The final estimated flow rate and its error were calculated as the mean and standard deviation within this plateau region.

Figure 6:
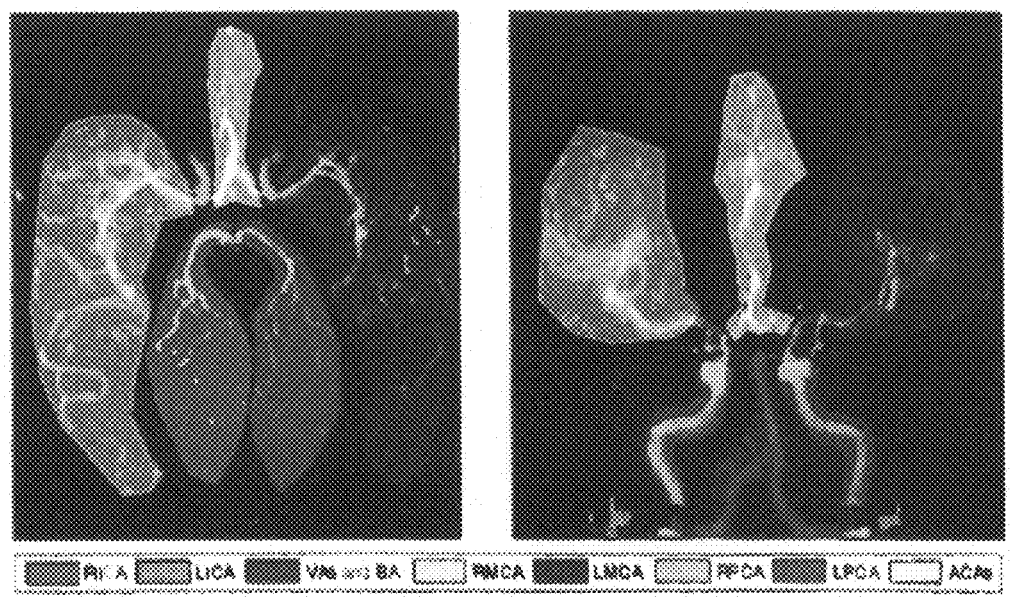
FIG. 6 depicts examples of manually drawn masks used for flow rate quantification in the major cerebral arteries overlaid on a map of $A_{tot}$ in a healthy volunteer in both transverse and coronal views.

Quantification was performed within a number of masks which were drawn manually for each data set (examples shown in FIG. 6). In the transverse view these encompassed the right and left middle cerebral arteries (RMCA and LMCA) and posterior cerebral arteries (RPCA and LPCA) along with both anterior cerebral arteries (ACAs), which were considered together due to their proximity. In the coronal view the MCAs and ACAs were also analyzed, but the more proximal coverage also allowed flow quantification in the right and left internal carotid arteries (RICA and LICA) and the combined flow in the vertebral and basilar arteries (VAs and BA). This larger mask ensured that the whole simulated bolus was contained within it. Note that the PCAs were not analyzed in the coronal view as they overlap considerably with other vessels, rendering attempts at quantification inaccurate.

Results: Kinetic Model Fits

Figure 7:
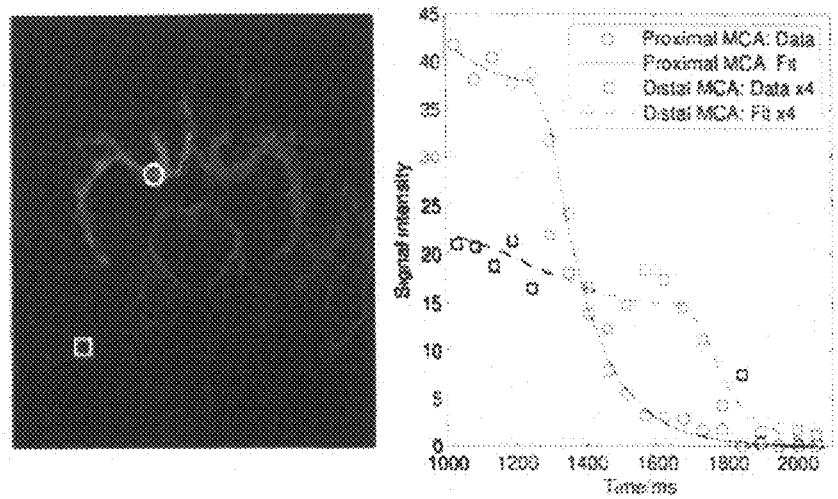
FIG. 7 depicts examples of the model fit to the data in a healthy volunteer using the transverse view.

Example fits of the kinetic model to the data are shown in FIG. 7 for one healthy volunteer transverse data set. The present model describes the data accurately in both proximal and distal regions, with examples shown here in the right middle cerebral artery (RMCA). Two locations in the proximal (circle) and distal (square) right MCA are overlaid on the color coded map of A (left): RICA=red, LICA=green, RVA=blue, LVA=purple.

The corresponding time series and model fit at these locations to the right ICA component are also shown (right). The time axis is relative to the start of the VEPCASL pulse train.

Figure 8:
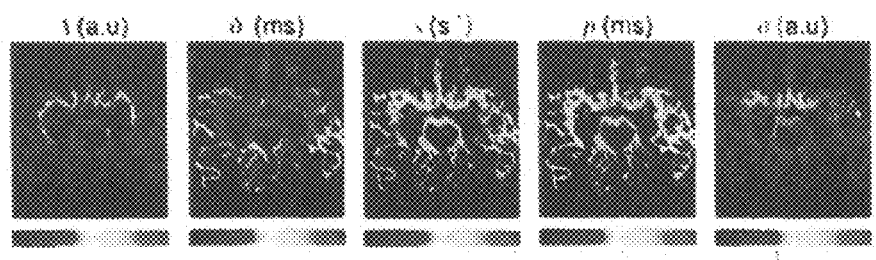
FIG. 8 depicts exemplary parameter maps generated by fitting the kinetic model of Eqn. 17 below to data from a healthy volunteer in the transverse view, averaged over the vascular components for clarity of presentation.

The parameter maps generated from the same data set (FIG. 8) show the expected patterns: A, which relates to blood volume, is high in the large proximal vessels, the blood arrival time, $\delta_t$, is extended in distal vessels and to some extent at the large vessel edges due to the laminar nature of the flow and the dispersion parameters indicate a higher degree of dispersion (low s and high p) in more distal vessels. Note that in some small distal vessels with late blood arrival s and p tend towards the mean values of their prior distributions. This is because less of the tail of the signal curve is present in the acquired data and thus less accurate dispersion parameter estimates can be achieved. The noise estimate, σ, is higher in a region in line with the large proximal vessels. This is probably due to ghosting artefacts across the phase-encode (left-right) direction resulting from the more pulsatile flow in these large vessels. Away from these areas σ is relatively constant as might be expected.

Results: Inflow Visualization

Figure 9:
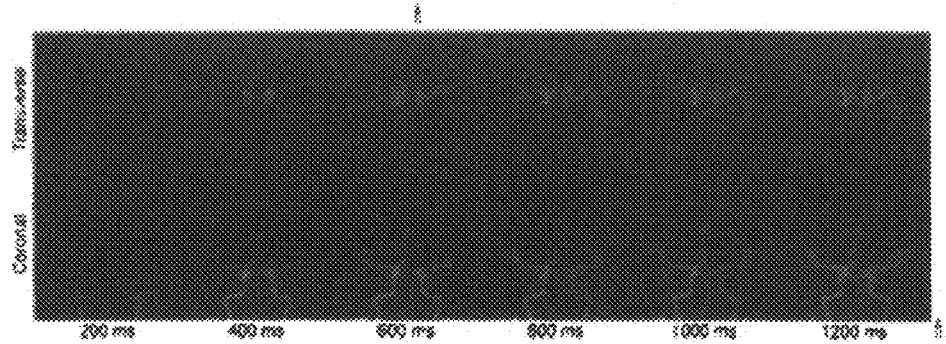
FIG. 9 depicts simulation of blood inflow: example frames in both a transverse and coronal view of the same subject generated using the kinetic model parameter estimates and assuming an infinitely long bolus duration with the simulation time shown underneath.

Examples of synthetic blood inflow visualization using the derived kinetic model parameters are given in FIG. 9, with attenuation due to $T_1$ decay and imaging RF pulses removed. This more intuitive way to display the data shows the expected patterns of inflow into the arterial tree and the later arrival of vertebral blood is clear in these images.

FIG. 9 also demonstrates the potential of this method to clearly identify unusual flow patterns within the cerebral vasculature. Note that this subject has non-standard flow patterns around the circle of Willis, including collateral flow from the LICA to the LPCA. This subject has little flow in the left vertebral artery and a partial fetal type circle of Willis (van Raamt et al., 2006) on the left side. In addition, the left anterior cerebral artery (LACA) is missing the A1 segment, meaning that both ACAs are supplied from the RICA via the anterior communicating artery.

Results: Relative Flow Rate Calculations

Figure 10:
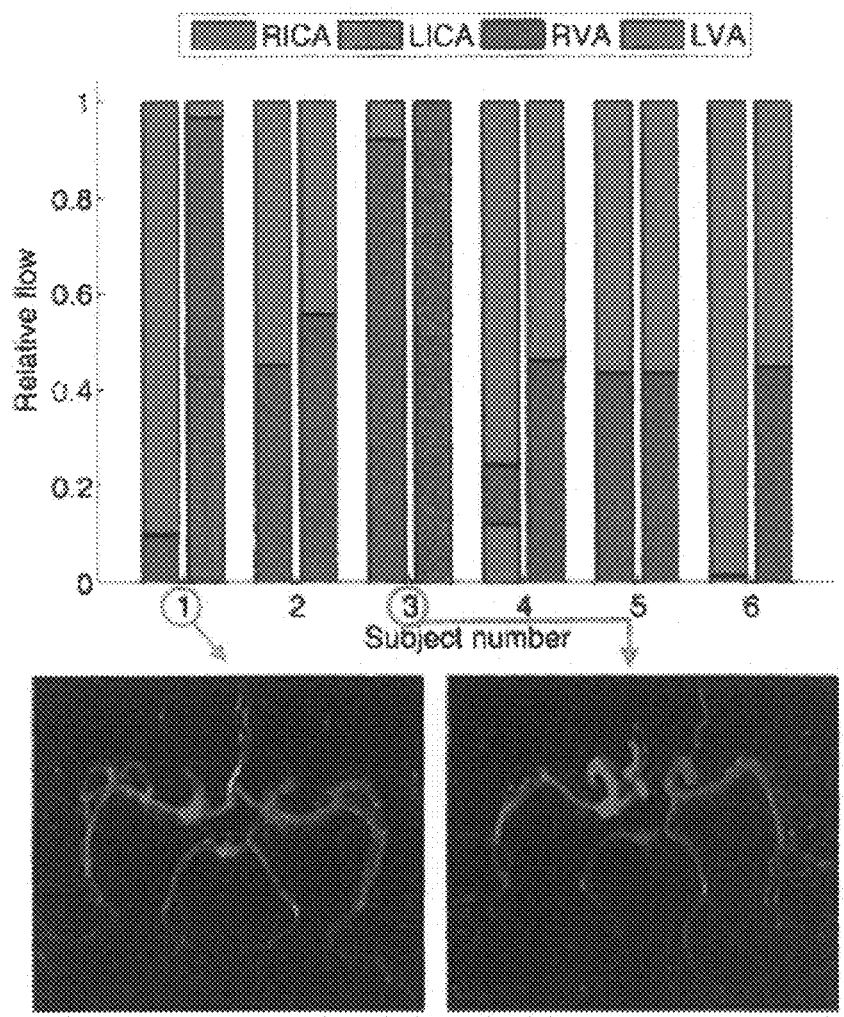
FIG. 10 depicts relative blood volume flow rate calculations in the posterior cerebral arteries, PCAs, of healthy volunteers in the transverse view.

Results from calculations of the relative blood volume flow rates in the PCAs of all healthy volunteers are shown in FIG. 10. The stacked bar chart shows the relative blood flow contributed by each of the feeding arteries (see legend) in both the RPCA (left bar) and LPCA (right bar) for each subject. Subjects 2, 4, 5 and 6 demonstrate the expected pattern where the majority of blood in each PCA originates approximately equally from the RVA and LVA. Subjects 1 and 3 show a considerable amount of collateral flow from the LICA to the LPCA via the left posterior communicating artery. The corresponding map of A is shown underneath, demonstrating clear filling of the left posterior communicating arteries. Interestingly the majority of the blood feeding each PCA for Subject 1 comes from the contralateral VA, as has been shown in a qualitative manner previously (Okell et al., 2010).

Results: Kinetic Model Fitting in the Patient with Moya-Moya Disease

Figure 11:
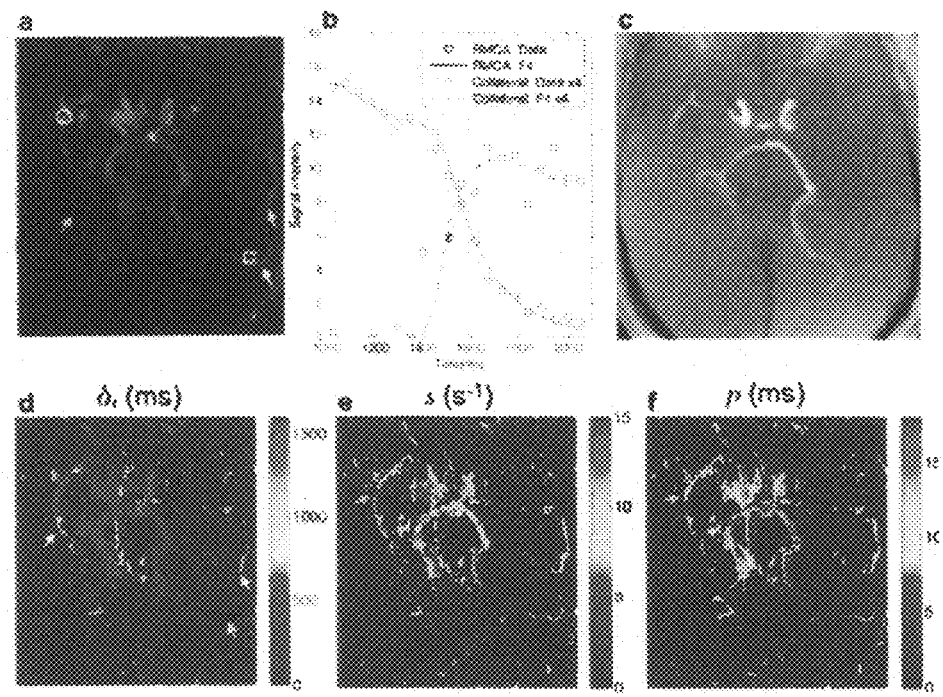
FIG. 11 depicts an exemplary fitting of the present model to transverse data from a patient with Moya-Moya disease: a color coded map of A in the transverse view (a) with two voxel locations in the right middle cerebral artery, RMCA, and a collateral vessel overlaid. The time series of the dominant vascular component and corresponding fit to the model in these locations is plotted in (b), with the collateral data and fit multiplied by four for clarity. The small collateral vessels are not visible in a time of flight (TOF) transverse maximum intensity projection of the same imaging region (c). Other parameter maps (showing only voxels where A>7 for visual clarity) are also shown (d-f).

FIG. 11 shows the result of an exemplary fitting of the present model in a patient with Moya-Moya disease, which is characterized by progressive stenosis of some of the cerebral arteries leading to the development of numerous collateral vessels (Vilela et al., 2005). Points of interest include: high level stenosis in both MCAs (purple arrows), the formation of small branching collateral vessels (green arrow), delayed arrival in the LICA relative to the RICA (red arrow), larger collaterals from the posterior circulation into the LMCA territory with very delayed arrival (yellow arrows) and a higher degree of dispersion (orange arrows) and late arrival (white arrow) in the distal RMCA compared to other vessels. The high degree of stenosis and extensive collateral formation typical of Moya-Moya disease are apparent in these images.

These findings agree well with the patient's x-ray DSA report, which states that high grade stenoses were observed in the right proximal middle cerebral artery and the left distal internal carotid artery along with considerable collateral formation. The model provides an accurate description of the data, even in voxels containing collateral vessels with extremely delayed arrival. The smaller collateral vessels are not visible in the TOF maximum intensity projection (MIP) of the same region and are also difficult to identify in the raw images (not shown). The source of blood to the larger collateral vessels feeding the LMCA territory is clearly visualized with this technique and the extended arrival time is very apparent in the map of $\delta_t$. Relative flow rate calculations indicate that 99% of the blood in these large collaterals originates in the RVA and only 1% from the LVA, although other small contributions may be present that do not survive the masking procedure. The blood in the RMCA distal to the significant stenosis shows both delayed arrival and a greater degree of dispersion relative to other vessels, suggesting that such parameters may be indicative of upstream disease.

The potential benefits of the inflow visualization are evident in this patient (FIG. 12) where the extended arrival time in collateral vessels leads to significantly attenuated signal due to $T_1$ decay and the imaging RF pulses. Note that different time scales were used to display the full range of information in each data set and the times shown are relative to the start of labeling. The late arrival of blood in collateral vessels is much clearer in the inflow simulation than the original data (yellow arrows) due to compensation for signal attenuation. The slightly later arrival of blood from the LICA compared to the RICA is also more apparent using inflow simulation (pink arrow). The inflow simulation shows these collateral vessels much more clearly, giving a less biased indication of the volume of blood flowing through each vessel. Differences in arrival time between the two ICAs are also more apparent in the simulation than the original data.

Results: Flow Rate Quantification Validation with a Flow Phantom

Figure 13:
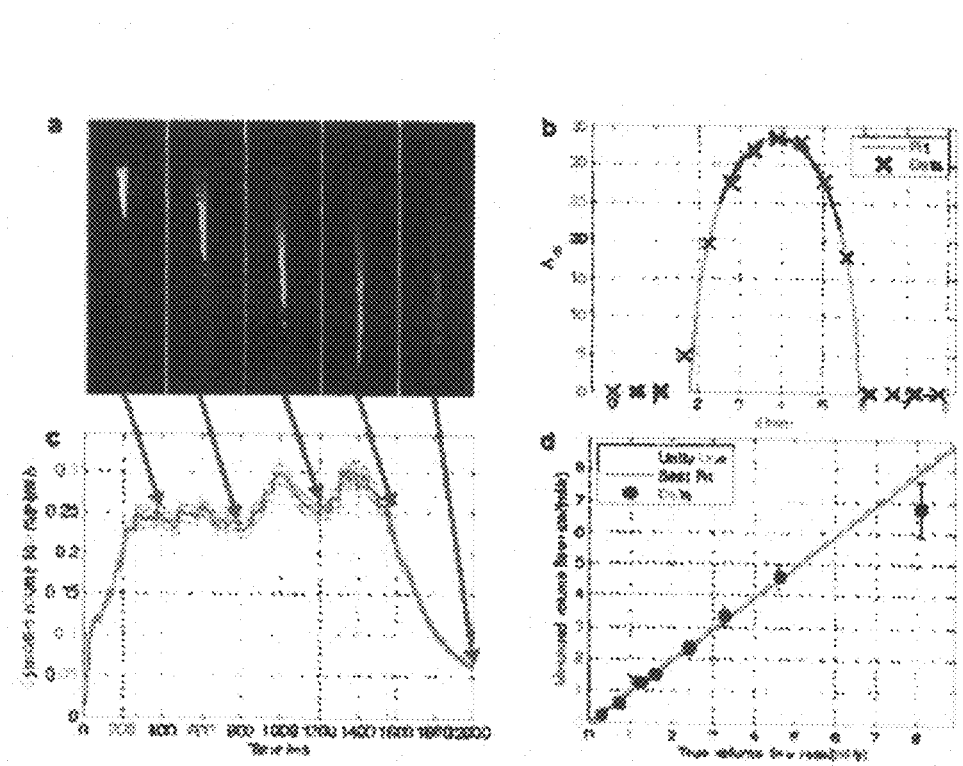
FIG. 13 depicts a validation of the quantification method in a flow phantom: (a) a series of images of the simulated signal, S', with the vessel mask overlaid (yellow tinted area) at different simulated time points (indicated by the arrows); (b) an example of the calibration method showing the fit of Eqn. 12 to a profile of $A_{tot}$ across one of the tubes; (c) the estimated volume flow rate at each time point (thick line) with error margins (thin lines) and the estimated plateau region (dashed lines); (d) the volume flow rate and its error calculated using the proposed method plotted against the true volume flow rate as measured during the experiment.

FIG. 13 shows the results of a flow phantom experiment. The simulated signal behaves as expected with the bolus travelling steadily downstream (flowing from the top of the figure to the bottom) and becoming more dispersed over time. The calibration method appears to work well with Eqn. 12 providing a good fit to the data. As predicted (see FIG. 5) the estimated volume flow rate reaches a plateau before falling at later simulated time points.

The volume flow rate estimated using the proposed method is very close to the true flow rate measured from the phantom outflow pipe during the experiment. Results for flow rates below about 4.5 ml/s are very close to the ideal unity line. The line of best fit has gradient 0.98±0.03 and intercept −0.04±0.02 ml/s. Note that FIGS. 13 (a) and (c) were generated using data where the true flow rate was 0.30 ml/s. The highest measured flow rate was somewhat underestimated, but the line of best fit ($\chi^2$=4.0) suggests that on average that the systematic underestimation of the volume flow rate is only 2±3% across the measured range.

As expected, the choice of r' had a negligible effect (≤2% change) on the estimated volume flow rates for r'≤10 ms. Thus, for the studies below we fixed r' at 1 ms.

Results: Absolute Flow Quantification in Healthy Volunteers

Figure 14:
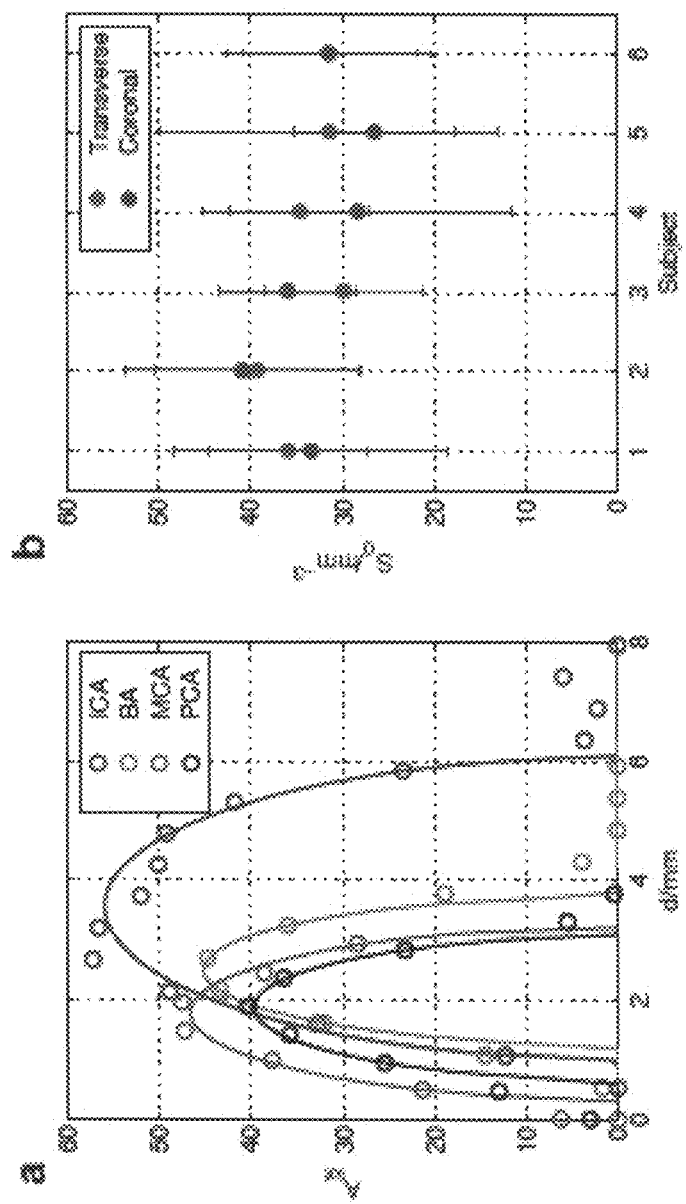
FIG. 14 depicts an exemplary signal calibration in healthy volunteers included in a study: (a) Example fit to Eqn. 12 in the C1 segment of the internal carotid artery from one subject; (b) mean and standard deviation of the calibration factor, $S_0$, across all ten measurements for all subjects in both transverse and coronal views.

Calibration results in the healthy volunteers are summarized in FIG. 14. As for the flow phantom, the calibration equation (Eqn. 12) appears to describe the data well. There is some variation in the calculated calibration factor over the ten measurements made for each data set, but the mean values appear to be relatively consistent across subjects and between transverse and coronal views despite potential differences in coil loading and subject positioning. This suggests that the calibration procedure is reasonably robust and therefore is unlikely to lead to gross errors in the absolute volume flow rates which depend upon it.

Figure 15:
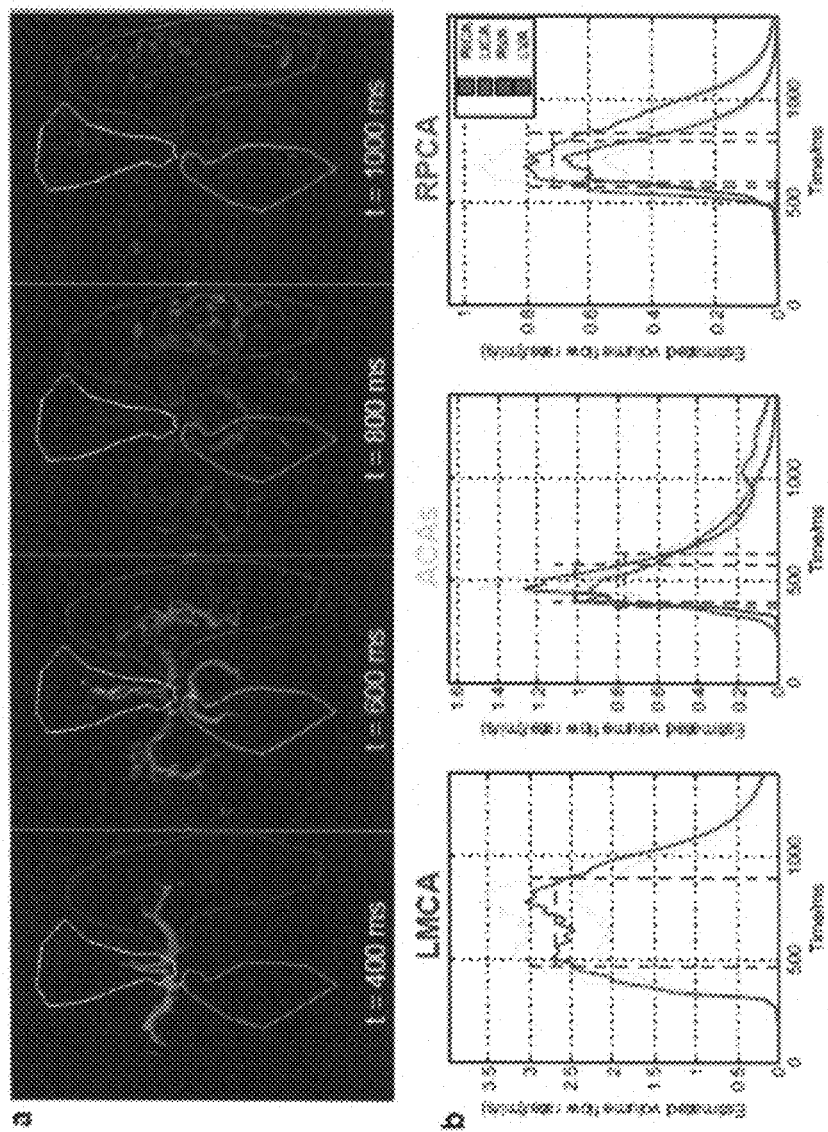
FIG. 15 depicts examples of flow quantification in the transverse view of one subject: (a) selected frames of the simulated signal, S', with overlaid masks of three example vessels (LMCA, ACAs and RPCA); and (b) the estimated blood volume flow rate over simulated time for each of the three masks.

Examples of flow rate quantification using transverse data from one healthy volunteer are given in FIG. 15. FIG. 15(a) depicts selected frames of the simulated signal S', with overlaid masks of three example vessels (LMCA, ACA's and RCPA). FIG. 15(b) depicts the estimated blood volume flow rate over simulated time for each of the three masks. The blood signal from each feeding artery is assigned a color in both the simulated signal images (a) and the flow rate plots (b) as shown in the legend. Note that by the time the simulated bolus reaches the circle of Willis there is already a considerable amount of dispersion which necessitates the use of large vessel masks to ensure the entire bolus is encompassed. In the LMCA the expected plateau behaviour is observed, in a similar manner to that seen in the flow phantom, which suggests that the kinetic model is describing the data well, despite the gap between the imaging region and the labeling plane in the transverse view which leads to a more complex correction for RF attenuation effects. In the RPCA, which is fed approximately equally from both vertebral arteries in the subject shown, similar behaviour is observed although the plateau region is quite small here. However, in the ACAs no plateau region is observed, meaning that it is likely that the simulated bolus starts to leave the imaging region or high signal mask before the whole bolus has washed in. Thus, the simulated bolus never lies entirely within the vessel mask so it is likely that the flow rate is underestimated here.

Figure 16:
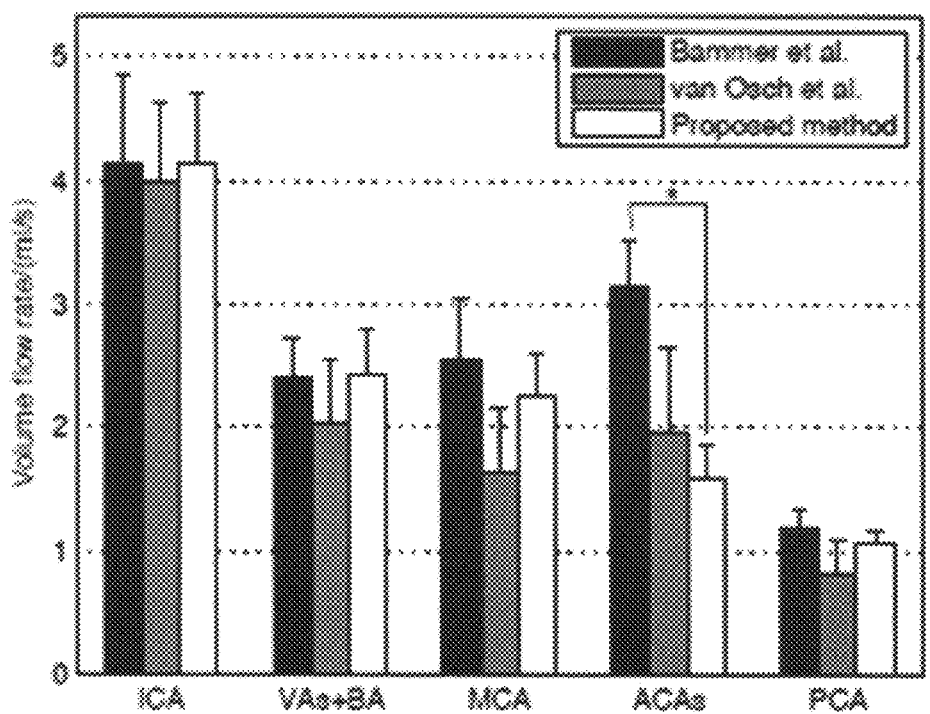
FIG. 16 depicts exemplary mean estimated blood volume flow rates averaged across all volunteers of the study and views.

A summary of the estimated volume flow rates summed over all volunteers, using both coronal and transverse data sets, is given in FIG. 16. The flow rate calculated for each feeding artery is shown in a separate color (see legend) and error bars represent the standard error in the mean across subjects. Values measured in healthy volunteers taken from studies by Bammer et al. (2007) (using phase-contrast MRA) and van Osch et al. (2006) (using pulsed ASL angiography) are plotted alongside for comparison. The values calculated using the proposed method generally agree well with those taken from these two papers. The only significant difference (as assessed using a two-tailed z-test with a significance level of 0.05 or 5%) occurred in the ACAs (p=0.0006) when compared to the measurements by van Osch et al. (2006).

Note that there are some differences in the measurement locations used in these studies. Van Osch et al. (2006) quote ICA and BA flow rates based on the sum of flow rates in vessels distal to the circle of Willis (e.g. ICAs=MCAs+ACAs), assuming no collateral flow. In this study the flow rate in the Vas and BA was estimated together, whereas Bammer et al. (2007) performed the measurement in a cross-section of the BA. In addition, Bammer et al. (2007) estimated the flow rate in each ACA separately rather than together, so we have doubled the value quoted in their study to allow comparison here. However, these differences are expected to have only a small effect on the comparisons.

Figure 17:
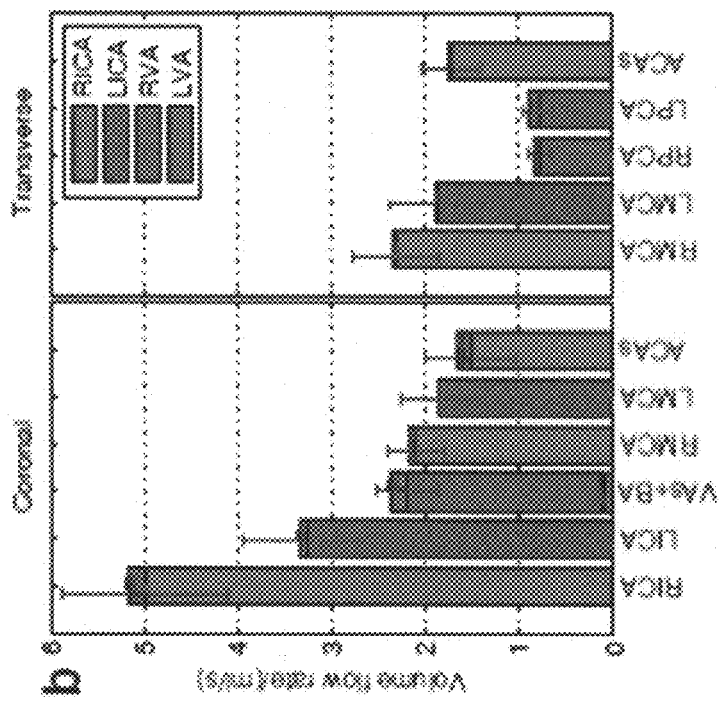
FIG. 17 is an example of the additional information gained by using a vessel-selective acquisition such as VEPCASL dynamic angiography in one healthy volunteer with non-standard flow patterns around the circle of Willis: (a) Color-coded map of the relative blood volume parameter, A; (b) The estimated volume flow rates in all vessel segments for this subject, in both coronal and transverse views, with the contribution from each feeding artery shown in a separate color (see legend).
Figure 17:
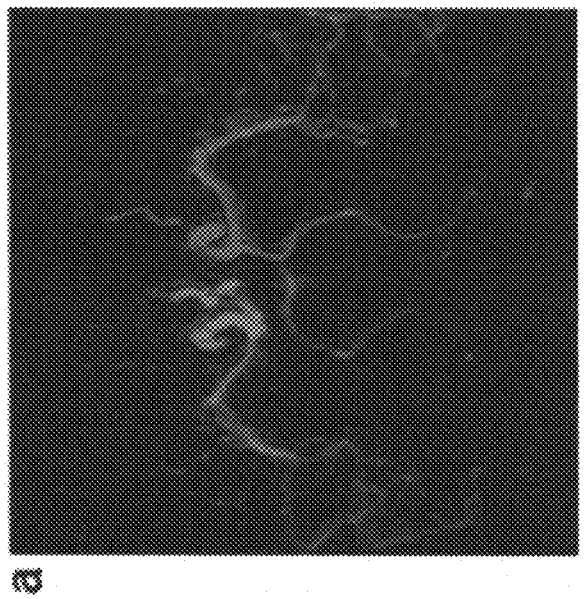

The use of VEPCASL dynamic angiography means that not only can the total flow rate in a given vessel segment be quantified, but the contribution from each feeding artery can be assessed. An example of the potential utility of this additional information is given in FIG. 17. In this subject both ACAs are fed by the RICA, there is very little blood originating from the LVA and there is also considerable collateral flow from the LICA into the LPCA. The RICA flow rate is considerably higher than the LICA, perhaps since it is feeding both ACA territories, although the difference is not statistically significant. There is some minor contamination of signals due to background noise or motion artefacts (e.g. the presence of apparent RVA signal in the RICA).

In order to test consistency, the total blood volume flow rate entering the circle of Willis, as measured in the ICAs, VAs and BA, should be approximately equal to that flowing out, as measured in the MCAs, ACAs and PCAs, with the exception of the loss of some blood through small branching arteries such as those supplying the cerebellum, deep grey matter or the eyes. Across all subjects and feeding arteries (24 in total) there were only three cases in which there was a significant difference between the input and output flow rates (i.e. p<0.05). One of these is the RVA of the subject shown in FIG. 17. On average output flow rates were lower than input flow rates by 0.6±0.7 ml/s (mean±standard deviation) there was no significant difference between the input and output flow rates (i.e. p>5%), although the output flow rates were generally lower.

Figure 18:
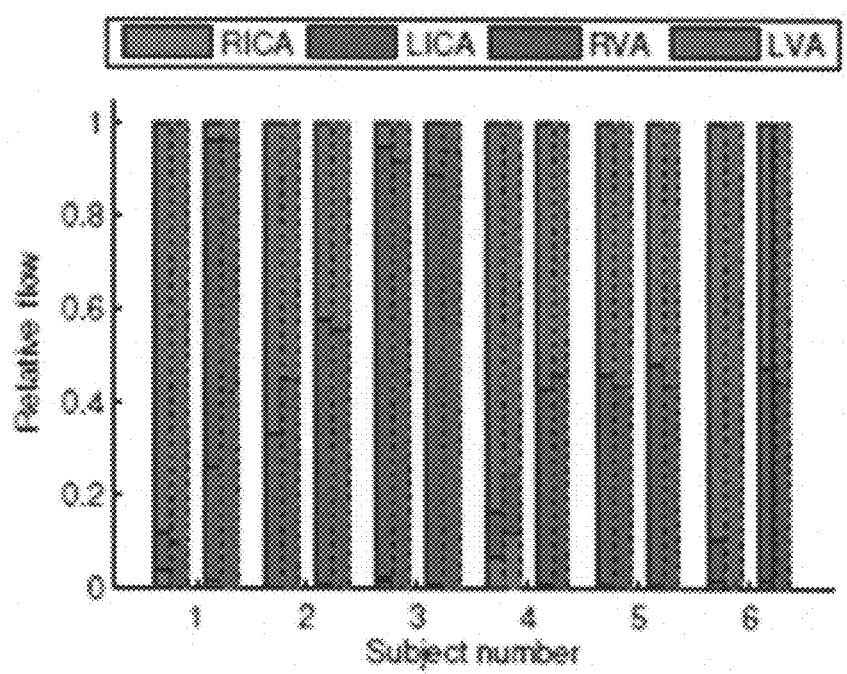
FIG. 18 is a comparison of relative blood volume flow rates from each feeding artery calculated using absolute flow rates (solid bars) or by summing A across a short vessel segment (dotted bars) in the PCAs of all subjects. For each subject the first pair of bars corresponds to the RPCA and the second pair to the LPCA. The relative contribution from each artery is color coded as before (see legend).

In a previous paper (Okell et al., 2012) we have shown that relative volume flow rates from each feeding artery can be calculated by summing the parameter A across small vessel masks in well-mixed downstream vessels. In the PCAs of the subjects used in this study, where considerable mixing of blood from feeding arteries occurs, there is good agreement between the relative flow rates calculated using this previous method, and the absolute flow rates measured for this study (see FIG. 18). The mean absolute difference between the two methods is 3±4%.

Discussion of Results

The systems and methods disclosed herein can be used to accurately describe the signal measured in dynamic angiographic data accounting for bolus dispersion, signal decay and effects due to the imaging method, allowing for the generation of parameter maps relating to blood volume, arrival time and dispersion. They allow the quantification of blood volume flow rates using dynamic angiographic data. They provide a means to create intuitive inflow visualization without confounding factors that attenuate the signal, and quantification of relative blood volume flow rates from each feeding artery. In addition, absolute quantification of blood volume flow rates can be performed, for example from each brain-feeding artery without the need for invasive procedures, ionising radiation or contrast agent. Their self-calibrating nature avoids the need for additional calibration scans.

An exemplary system and method is demonstrated using 2D vessel-encoded pseudo-continuous arterial spin labeling (VEPCASL) dynamic angiographic data, although this approach can also be used with 3D data and other angiographic techniques. The ability to quantify flow rates from each feeding artery is of use in a number of situations, such as the assessment of collateral blood flow, the identification of vascular territories that are at risk of ischemic damage in patients with steno-occlusive disease and the evaluation of arteriovenous malformations.

FIGS. 7 and 11 demonstrate that the present systems and methods accurately describe the angiographic signal in both proximal and distal arteries of healthy volunteers and a patient with Moya-Moya disease. These fits also highlight the importance of accounting properly for the earliest arrival of blood in the imaging region, which causes the early part of these curves to level out to a relatively constant value prior to the bolus washing out of the voxel. Failing to account for this effect may lead to overestimation of the relative blood volume within the voxel.

The derived parameter maps (FIG. 8) show the expected patterns in the healthy volunteers. Differences from these patterns are seen in the patient with Moya-Moya disease (FIG. 11). The delayed arrival of the blood from the LICA relative to the RICA may be due to the greater degree of stenosis in the LMCA than the RMCA, leading to greater resistance to blood flow. The increased level of dispersion in the distal RMCA may also indicate upstream disease. It is worth noting that the concentration of labeled blood and its fast passage through large arteries enables a more accurate assessment of the dispersion parameters than may be possible with standard arterial spin labeling methods that focus on tissue perfusion. As mentioned above, dispersion parameters cannot be accurately determined in voxels with late arrival since the tail of the distribution is not visible in the acquired time window. Experiments using this type of modeling approach and a longer acquisition window may help determine appropriate dispersion parameters in small distal vessels closer to the capillary bed, enabling more accurate quantification of cerebral blood flow or comparison across a range of dispersion models.

The simulated inflow images exemplified in FIGS. 9. and 12 allow a more intuitive way of visualizing the data that is likely to appeal to clinicians who are familiar with x-ray DSA. The removal of effects due to T1 decay and the imaging RF pulses means the signal observed truly relates to the volume of labeled blood present, preventing bias in the image interpretation. This effect is clear from the improved visibility of the collateral vessels with greatly delayed arrival in the patient data shown here. These vessels are poorly visualized using TOF due to the residual signal from overlying tissue (which is subtracted out in the VEPCASL angiographic method) and saturation of slow flowing spins which spend a significant amount of time in the imaging region. Optimization of the TOF protocol for such patients may result in improved visualization of these smaller vessels but some level of static tissue signal and in-plane lumen saturation will always remain.

An additional benefit of the inflow visualization method is reduction in the amount of noise in the data from the smooth nature of the fitted curve, but without the loss of temporal fidelity which would result from time series smoothing. The ability to reconstruct such images at any desired temporal resolution is also advantageous, although ultimately it is limited by the temporal resolution of the acquired data.

The ability to quantify the relative flow rates in distal vessels due to each feeding artery (FIG. 10) may be of use in patient groups, particularly those with stenosis proximal to the circle of Willis. For example, the decision to perform endovascular therapy on such a stenosed artery can be informed by the relative importance of collateral flow from other vessels. The fact that this imaging protocol identified normal variants of flow patterns in healthy volunteers suggests that it may provide useful clinical information in patients with cerebrovascular disease.

The ability to calibrate the measured signal against blood volume using the same data set is important for 2D projection methods such as x-ray DSA. It also removes the need for additional calibration scans, which is advantageous in a busy clinical protocol. For the 2D data sets considered here the calibration equation (Eqn. 12) describes the data well in most cases (FIGS. 13b and 14a), suggesting that the approximation of circular vessel cross-sections is reasonable, at least in the arteries of healthy volunteers considered here. However, a vessel with an elliptical cross-section would give a curve of the same shape but give an incorrect value for $S_0$ estimates within each subject, but performing a sufficient number of calibration steps in different arteries should help to average out such effects. In addition, estimates of $S_0$ could be skewed by incomplete filling of the arterial segment being used for calibration during the imaging time, leading to misestimation of the vessel diameter, although this should not be the case for the proximal vessel segments chosen in this study.

The fact that the calibration factor is fairly consistent across individuals and views (FIG. 14) also suggests that the method is reasonably robust. This raises the possibility of using a single calibration factor for all subjects. However, variations in subject positioning within the coil, the coil loading and PCASL inversion efficiency could all affect the value of $S_0$ appropriate for each subject, so a subject-specific calibration factor is likely to be more accurate.

In a flow phantom it was shown that the estimated volume flow rate evaluated over a range of simulated time points forms the expected plateau region (FIG. 13c). This indicates that the VEPCASL dynamic angiography kinetic model describes well the signal attenuation due to $T_1$ and RF effects since poor modeling of these factors would lead to an increasing or decreasing estimated flow rate over time. Averaging over this plateau region allows a more robust estimate of the flow rate to be obtained than taking a single time point alone. In addition, there is good agreement between the values estimated using this method and those measured directly using the flow phantom outflow pipe, particularly for flow rates below about 4.5 ml/s (FIG. 13d), which corresponds to those commonly found in the cerebral vasculature, with no significant systematic error (2±3%).

The flow rate quantification appears to also work well in most of the cerebral vessels proximal and distal to the circle of Willis (see FIG. 15), yielding results that are generally consistent with the literature. Although results for only two other papers are plotted in FIG. 16, these are similar to those found in other studies (e.g. see Hendrikse et al. (2005) and Stock et al. (2000)). However, the flow rate in the ACAs appears to be underestimated. This is probably because branches of the ACAs were not captured within the imaging region and also perhaps that they are relatively small so they might have been excluded from the high signal mask. Both of these factors mean the whole simulated bolus was not captured within the vessel mask so the flow rate was underestimated.

The subject show in FIG. 11 has a higher measured flow rate in the RICA than in the LICA. This subject has a missing A1 segment in their left ACA, meaning that all the blood feeding both ACAs comes from the RICA. Subjects with this variant of the circle of Willis have been shown previously to have increased ICA flow rate on the contralateral side (Hendrikse et al., 2005). This perhaps contributed to the average RICA flow rate being higher than the LICA flow rate although the difference was not significant (p=0.14).

The fact that the total blood flow rate distal to the circle of Willis was smaller than that measured in proximal vessels is not surprising, since some blood is diverted to the cerebellum, brainstem and deep grey matter before flowing into the main branches of the MCAs, ACAs and PCAs. The significant difference in a few cases, such as the RVA flow rate of the subject shown in FIG. 11, could also be due to not enough of the distal vessels being present in the imaging region for accurate quantification and/or exclusion of small vessel branches from the high signal mask.

Figure 12:
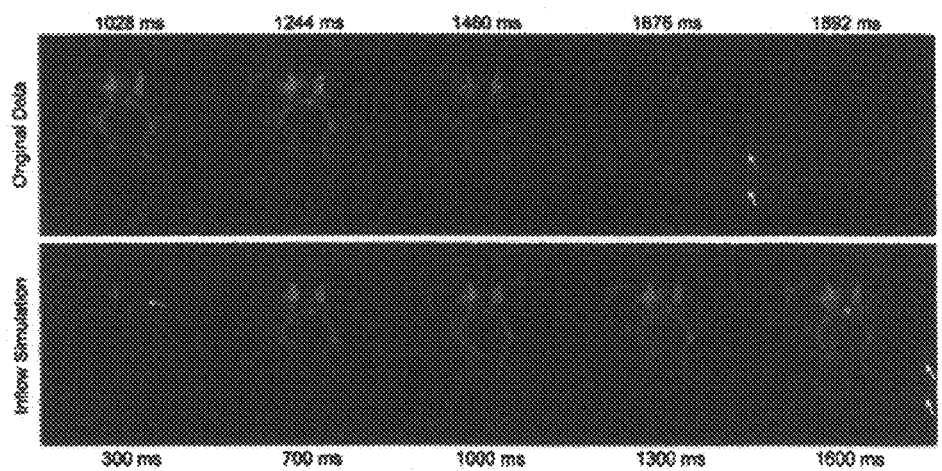
FIG. 12 depicts a comparison between the original unprocessed data (top) and simulated inflow (bottom) which corrects for $T_1$ decay and imaging RE effects in the patient with Moya-Moya disease.

FIG. 12 shows that our previous method (Okell et al., 2012) for calculating relative blood volume flow rates from each of the feeding arteries in well-mixed downstream vessels gives very similar results to the absolute quantification. This may be helpful in cases where this relative flow information is the main interest and a quick analysis is required or the vessel segment of interest is too short to encompass the dispersed simulated bolus.

To our knowledge there is only one other study where quantitative blood volume flow rates have been derived from ASL-based angiographic data: van Osch et al., 2006 used a vessel-selective or non-selective pulsed ASL preparation followed by a segmented-EPI Look-Locker readout of the circle of Willis. Flow quantification was achieved using an arterial input function measured in a separate scan just proximal to the circle of Willis in combination with the summed signal across a vessel mask of interest distal to the circle of Willis. Accurate flow measurements were made with this method, despite imaging at only 1.5T, and validated against phase-contrast angiographic data. However, that technique could not be applied directly to data acquired with continuous or pseudo-continuous labeling unless a short labeling duration was used and the labeling plane was positioned very proximally to ensure that the early part of the AIF could be measured. This would reduce the volume of labeled blood being produced and lead to greater $T_1$ decay before the blood reaches the arteries of interest, leading to reduced SNR. In addition, this would restrict the optimal positioning of the labeling plane for vessel-encoding and potentially lead to problems with off-resonance effects further from the scanner isocentre.

Our present systems and methods have the advantage of being applicable to modalities in which such an absolute AIF cannot be measured. They also have the advantages of not requiring the measurement of an arterial input function (for angiographic methods where the input function is known, such as VEPCASL dynamic angiography) or the assumption of plug flow through the vessel mask of interest. In addition, VEPCASL allows the creation of a bolus with a longer duration, leading to higher SNR than pulsed ASL, and vessel-selective labeling is not restricted to cases where a 3D slab can be positioned over a long segment of the artery of interest whilst excluding all others. However, the explicit modeling of the summed signal within the vessel mask enabled flow measurements to be made in smaller vessel segments than those used in our study.

The other commonly used method for flow rate quantification within arteries is phase-contrast MRA. Although 3D information can be obtained with this method and flow quantification performed across very short vessel segments, there is a lack of information regarding the arterial source of the flow. In addition, to achieve good coverage of the vessels scan times can be long: approximately 10 minutes to cover a 48 mm slab centred on the circle of Willis using a parallel imaging factor of three (Bammer et al., 2007). This would be considerably longer to extend coverage to allow assessment of the vertebral arteries also. Although the acquisition method presented in this paper is not very rapid (10 minutes per view), there is considerable scope for acceleration using parallel imaging (Pruessmann et al., 1999; Griswold et al., 2002), compressed sensing (Lustig et al., 2007) and the use of a balanced steady-state free precession readout (Okell et al., 2011). In addition, the analysis approach presented here is applicable to more rapid acquisition methods, such as x-ray DSA. Finally, partial volume effects can lead to the underestimation of flow rates in phase-contrast MRA (Bammer et al., 2007), particularly in small intra-cranial vessels. With ASL-based methods static tissue subtracts away, leaving a signal which only depends on the volume of blood present within the voxel, so partial volume effects do not affect the flow rate quantification.

It is worth noting that an alternative way to calculate the volume flow rate using our proposed method would be to simulate the signal using an infinite bolus duration. Once the simulated bolus enters the vessel mask of interest the slope of the summed signal across the mask could be used to calculate the volume flow rate. This is equivalent to the short simulated bolus method used in this study, although the identification of an appropriate region over which the flow rate can be measured is less obvious than identification of the plateau region used here.

System and Apparatus

Figure 19:
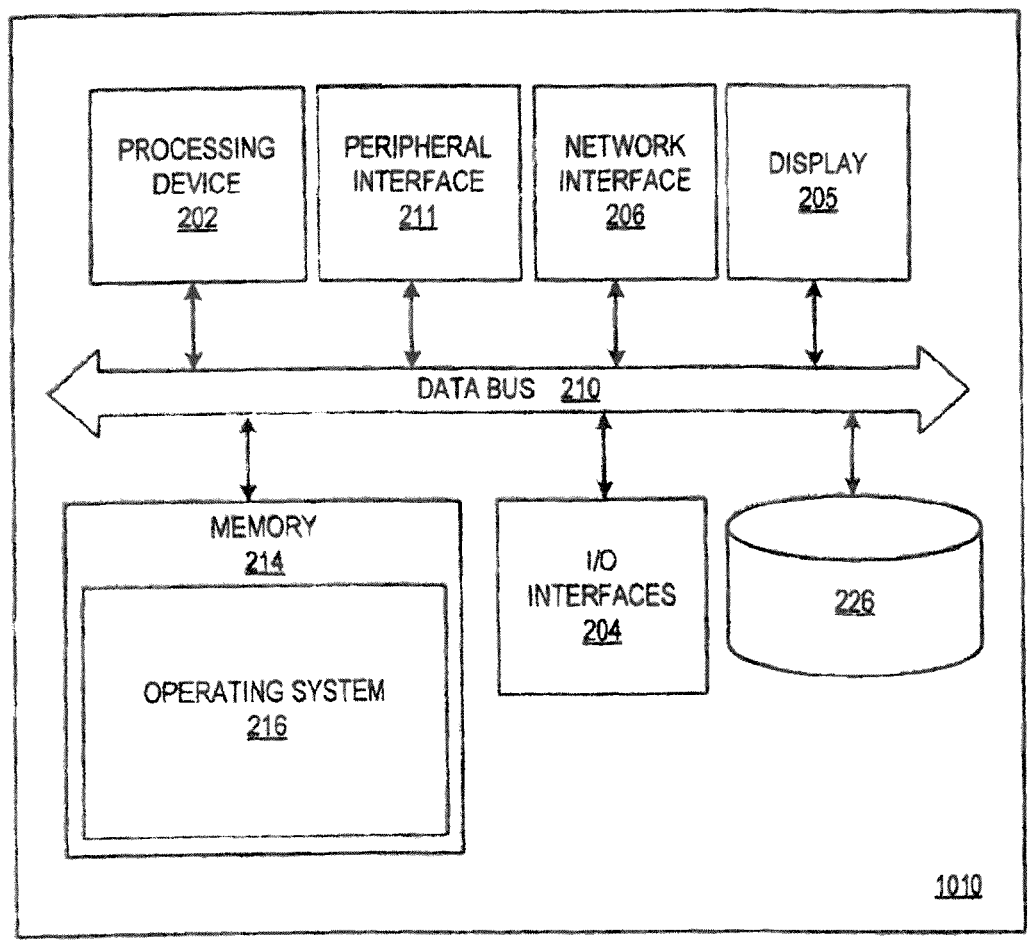
FIG. 19 is a schematic block diagram of an apparatus in which embodiments of the present systems and methods for quantification of blood volume flow rates from dynamic angiography data disclosed herein may be implemented.

Reference is now made to FIG. 19, which depicts an apparatus 1010 in which the systems and methods for providing blood flow rate quantification of dynamic angiographic data described herein may be implemented. The apparatus 1010 may be embodied in any one of a wide variety of wired and/or wireless computing devices, multi-processor computing device, and so forth. As shown in FIG. 19, the apparatus 1010 comprises memory 214, a processing device 202, one or more input/output interfaces 204, a network interface 206, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the systems and methods for quantification of arterial spin labeling dynamic angiography described herein. In accordance with such embodiments, the application specific software is stored in memory 214 and executed by the processing device 202. One of ordinary skill in the art will appreciate that the memory 214 can, and typically will, comprise other components which have been omitted for purposes of brevity.

The one or more input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, a touch screen or other display device.

In an embodiment of this disclosure, a non-transitory computer-readable medium stores programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 19, network interface device 206 comprises various components used to transmit and/or receive data over a network environment. For example, the network interface 206 may include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 may communicate with one or more computing devices (not shown) via the network interface 206 over the network 118 (not shown). The apparatus 1010 may further comprise mass storage 226. The peripheral 211 interface supports various interfaces including, but not limited to IEEE-1394 High Performance Serial Bus (Firewire), USB, a serial connection, and a parallel connection.

The apparatus 1010 shown in FIG. 19 may be embodied, for example, as a magnetic resonance apparatus, which includes a processing module or logic for performing conditional data processing, and may be implemented either off-line or directly in a magnetic resonance apparatus. For such embodiments, the apparatus 1010 may be implemented as a multi-channel, multi-coil system with advanced parallel image processing capabilities, and direct implementation makes it possible to generate images, for example, immediate T1 maps, available for viewing immediately after image acquisition, thereby allowing re-acquisition on-the-spot if necessary. Examples of apparatus in which the present systems and methods may be implemented are described in U.S. Pat. No. 5,993,398 and U.S. Pat. No. 6,245,027 and U.S. Publication No. 2011/0181285, which are incorporated by reference as if fully set forth herein.

The flow chart of FIG. 2 shows an example of functionality that may be implemented in the apparatus 1010 of FIG. 19. If embodied in software, each block shown in FIG. 2 may represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 19) in a computer system or other system. The machine code may be converted from the source code, etc. If embodied in hardware, each block may represent a circuit or a number of interconnected circuits to implement the specified logical function(s).

Although the flowchart of FIG. 2 shows a specific order of execution, it is understood that the order of execution may differ from that which is depicted. For example, the order of execution of two or more blocks may be scrambled relative to the order shown. Also, two or more blocks shown in succession in FIG. 2 may be executed concurrently or with partial concurrence. Further, in some embodiments, one or more of the blocks shown in FIG. 2 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

TABLE 1

| Symbol | Description |
|---|---|
| Generic Kinetic Model Parameters | |
| t | Time |
| S(t) | Signal intensity in a given voxel |
| $c_{in}(t)$ | Relative tracer concentration in a proximal vessel |
| $\Delta t$ | Blood transit time from a proximal artery to the voxel [$\delta_t$] |
| t' | Time delay due to dispersion [$t_d$] |
| D(t') | Dispersion kernel |
| T($\Delta t$, t', t) | Signal attenuation due to tracer decay |
| $\Psi(\Delta t, t', t)$ | Signal attenuation due to the imaging method [R] |
| $\upsilon$ | Volume of blood within vessels in the voxel |
| $S_0$ | Calibration factor: the signal intensity per unit blood volume |
| A | Scaling factor proportional to blood volume (A = $S_0\upsilon$) |
| Specific Kinetic Model Parameters Used In This Paper | |
| $\tau$ | VEPCASL labeling duration |
| p | Dispersion kernel time to peak |
| s | Dispersion kernel sharpness |
| $\Delta t_{mia}$ | Time at which labeled blood first arrives in the imaging region [$\delta_{t, min}$] |
| Parameters Used For Calibration | |
| $A_{tot}$ | Sum of .4 across all vascular components (if modelled separately) |
| $\Delta x, \Delta y, \Delta z$ | Voxel dimensions |
| $\bar{d}$ | Vessel diameter |
| d | Distance perpendicular to the vessel direction |

TABLE 1-continued

| Symbol | Description |
|---|---|
| $d_0$ | Location of the centre of the vessel |
| Parameters Used For Flow Rate Quantification | |
| $F_g$ | Volume flow rate of blood in vessel g |
| $V_g$ | Volume of labeled blood which flows into vessel g |
| $S'$ | Signal simulated in the absence of attenuating effects |
| $\tau'$ | Simulated bolus duration |

A description of the mathematical symbols used in this paper. Where symbols differ from Okell et al. (2012) the equivalent is shown in square brackets. Symbols with a hat (omitted here) represent estimated parameter values.

REFERENCES

[1] Liebeskind D S. Collateral circulation. Stroke 2003; 34:2279-84.
[2] Bendszus M, Koltzenburg M, Burger R, Warmuth-Metz M, Hofmann E, Solymosi L. Silent embolism in diagnostic cerebral angiography and neurointerventional procedures: a prospective study. Lancet 1999; 354:1594-7.
[3] Kaufmann T J, Huston, 3rd J, Mandrekar J N, Schleck C D, Thielen K R, Kallmes D F. Complications of diagnostic cerebral angiography: evaluation of 19,826 consecutive patients. Radiology 2007; 243:812-9.
[4] Masaryk T J, Modic M T, Ross J S, Ruggieri P M, Laub G A, Lenz G W, Haacke E M, Selman W R, Wiznitzer M, Harik S I. Intracranial circulation: preliminary clinical results with three-dimensional (volume) MR angiography. Radiology 1989; 171:793-9.
[5] Hendrikse J, van der Grond J, Lu H, van Zip P C, Golay X. Flow territory mapping of the cerebral arteries with regional perfusion MRI. Stroke 2004; 35:882-7.
[6] Werner R, Norris D G, Alfke K, Mehdorn H M, Jansen O. Continuous artery-selective spin labeling (CASSL). Magn Reson Med 2005; 53:1006-12.
[7] Günther M. Efficient visualization of vascular territories in the human brain by cycled arterial spin labeling MRI. Magn Reson Med 2006; 56:671-5.
[8] Wong E C. Vessel-encoded arterial spin-labeling using pseudo-continuous tagging. Magn Reson Med 2007; 58:1086-91.
[9] Dai W, Robson P M, Shankaranarayanan A, Alsop D C. Modified pulsed continuous arterial spin labeling for labeling of a single artery. Magn Reson Med 2010; 64:975-82.
[10] Helle M, Norris D G, Rüfer S, Alfke K, Jansen O, van Osch M J P. Superselective pseudo-continuous arterial spin labeling. Magn Reson Med 2010; 64:777-86.
[11] Chng S M, Petersen E T, Zimine I, Sitoh Y Y, Lim C C T, Golay X. Territorial arterial spin labeling in the assessment of collateral circulation: comparison with digital subtraction angiography. Stroke 2008; 39:3248-54.
[12] Wu B, Wang X, Guo J, Xie S, Wong E C, Zhang J, Jiang X, Fang J. Collateral circulation imaging: MR perfusion territory arterial spin-labeling at 3T. AJNR Am J Neuroradiol 2008; 29:1855-60.
[13] Okell T W, Chappell M A, Woolrich M W, Günther M, Feinberg D A, Jezzard P. Vesselencoded dynamic magnetic resonance angiography using arterial spin labeling. Magn Reson Med 2010; 64:698-706.
[14] Günther M, Warmuth C, Zimmer C. Sub-millimeter dynamic spin labeling cerebral 2D-angiography with 40 ms temporal resolution. In: Proceedings of the 10th Annual Meeting of ISMRM, Honolulu, Hi., 2002. p. 1100.
[15] Sallustio F, Kern R, Günther M, Szabo K, Griebe M, Meairs S, Hennerici M, Gass A. Assessment of intracranial collateral flow by using dynamic arterial spin labeling MRA and transcranial color-coded duplex ultrasound. Stroke 2008; 39:1894-7.
[16] Vilela P, Goulao A. Ischemic stroke: carotid and vertebral artery disease. Eur Radiol 2005; 15:427-33.
[17] Buxton R B, Frank L R, Wong E C, Siewert B, Warach S, Edelman R R. A general kinetic model for quantitative perfusion imaging with arterial spin labeling. Magn Reson Med 1998; 40:383-96.
[18] Hrabe J, Lewis D P. Two analytical solutions for a model of pulsed arterial spin labeling with randomized blood arrival times. J Magn Reson 2004; 167:49-55.
[19] Rausch M, Scheffler K, Rudin M, Radü E W. Analysis of input functions from different arterial branches with gamma variate functions and cluster analysis for quantitative blood volume measurements. Magn Reson Imaging 2000; 18:1235-43.
[20] Macintosh B J, Sideso E, Donahue M J, Chappell M A, Günther M, Handa A, Kennedy J, Jezzard P. Intracranial hemodynamics is altered by carotid artery disease and after endarterectomy: a dynamic magnetic resonance angiography study. Stroke 2011; 42:979-84.
[21] Lu H, Clingman C, Golay X, van Zijl P C. Determining the longitudinal relaxation time (T1) of blood at 3.0 Tesla. Magn Reson Med 2004; 52:679-82.
[22] Günther M, Bock M, Schad L R. Arterial spin labeling in combination with a Look-Locker sampling strategy: inflow turbo-sampling EPI-FAIR (ITS-FAIR). Magn Reson Med 2001; 46:974-84.
[23] Petersen E T, Lim T, Golay X. Model-free arterial spin labeling quantification approach for perfusion MRI. Magn Reson Med 2006; 55:219-32.
[24] Walsh D O, Gmitro A F, Marcellin M W. Adaptive reconstruction of phased array MR imagery. Magn Reson Med 2000; 43:682-90.
[25] Chappell M A, Okell T W, Jezzard P, Woolrich M W, Payne S J. Fast analysis of vessel encoded ASL perfusion and angiographic images for clinical applications. In: Proceedings 19th Scientific Meeting, ISMRM, Montreal, 2011. p. 366.
[26] Chappell M A, Okell T W, Jezzard P, Woolrich M W. A general framework for the analysis of vessel encoded arterial spin labeling for vascular territory mapping. Magn Reson Med 2010; 64:1529-39.
[27] Zhang Y, Brady M, Smith S. Segmentation of brain MR images through a hidden markov random field model and the expectation-maximization algorithm. IEEE Trans Med Imaging 2001; 20:45-57.
[28] Jenkinson M, Bannister P, Brady M, Smith S. Improved optimization for the robust and accurate linear registration and motion correction of brain images. NeuroImage 2002; 17:825-841.
[29] van Raamt A F, Mali W P T M, van Laar P J, van der Graaf Y. The fetal variant of the circle of willis and its influence on the cerebral collateral circulation. Cerebrovasc Dis 2006; 22:217-24.
[30] Warmuth C, Ruping M, Forschler A, Koennecke H C, Valdueza J M, Kauert A, Schreiber S J, Siekmann R, Zimmer C. Dynamic spin labeling angiography in extracranial carotid artery stenosis. AJNR Am J Neuroradiol 2005; 26:1035-43.
[31] van Osch M J, Hendrikse J, Golay X, Bakker C J, van der Grond J. Non-invasive visualization of collateral blood flow patterns of the circle of willis by dynamic MR angiography. Med Image Anal 2006; 10:59-70.
[32] MacKay D J C. Probable networks and plausible predictions—a review of practical bayesian methods for supervised neural networks. Network-Computation In Neural Systems 1995; 6:469-505.
[33] MacKay D J C, "Information theory, inference, and learning algorithms". Cambridge University Press, Cambridge, UK, 2003.
[34] Yuen K V, "Bayesian methods for structural dynamics and civil engineering". JohnWiley and Sons, Singapore, 2010.

What is claimed:

1. A method for quantification of blood volume flow rates within a vessel mask including blood vessels of interest within a subject, from dynamic angiography data, comprising the steps of:
   A. Acquiring dynamic angiographic data which covers the blood vessels of interest in a subject;
   B. Fitting a kinetic model to the dynamic angiographic data in each voxel or a subset of voxels deemed to contain the major blood vessels to derive parameter maps relating to relative blood volume, blood arrival time and dispersion of a blood bolus;
   C. Determining a calibration factor using the dynamic angiographic data and using the calibration factor to convert relative blood volume in each voxel or subset of voxels to an absolute blood volume;
   D. Using the derived parameter maps to simulate over a number of time points an expected signal that would arise from a bolus of labeled blood in the absence of signal decay;
   E. Summing the simulated signal within the vessel mask of interest and converting the summed signal into an estimate of absolute blood volume within the vessel mask using the calibration factor at each simulated time point; and
   F. Determining an absolute blood volume flow rate within the vessel mask of interest from the blood volume of step E and the simulated expected signal that would arise from a bolus of labeled blood at each simulated time point.

2. The method of claim 1, wherein the dynamic angiographic data is acquired by providing a medical imaging device, positioning the subject in association with the medical imaging device, and using the medical imaging device to acquire the data.

3. The method of claim 1, further including use of the parameter maps to simulate blood flow at any desired time points in the absence of signal decay/attenuation for unbiased data visualization.

4. The method of claim 3, wherein the desired time points include blood arrival to the vessel mask.

5. The method of claim 1, when applied to artery-specific data, further including determination of the relative blood volume flow rates from each feeding artery in well-mixed vessel segments.

6. The method of claim 1, further including the step of assessment of time points during which the simulated bolus data lies entirely within a vessel mask of interest to obtain estimates of the blood volume flow rate.

7. A system comprising
   at least one computing device;
   at least one application executable in the at least one computing device, the at least one application comprising logic that:
A. acquires dynamic angiographic data which covers the blood vessels of interest in a subject;
B. fits a kinetic model to the dynamic angiographic data in each voxel or a subset of voxels deemed to contain the major blood vessels to derive parameter maps relating to relative blood volume, blood arrival time and dispersion of a blood bolus;
C. determines a calibration factor and using the calibration factor to convert relative blood volume in each voxel or subset of voxels to an absolute blood volume;
D. uses the derived parameter maps to simulate over a number of time points an expected signal that would arise from a bolus of labeled blood in the absence of signal decay;
E. sums the simulated signal within a vessel mask of interest and converting the summed signal into an estimate of absolute blood volume within the vessel mask using the calibration factor at each simulated time point; and
F. determines an absolute blood volume flow rate within the vessel mask of interest from the blood volume of step E and the simulated expected signal that would arise from a bolus of labeled blood at each simulated time point.

8. The method of claim 7, wherein the logic acquires the dynamic angiographic data from a medical imaging device, wherein the subject is positioned in association with the medical imaging device, and the medical imaging device is used to acquire the data.

9. The system of claim 7, wherein the logic uses the parameter maps to simulate blood flow at any desired time points in the absence of signal decay/attenuation for unbiased data visualization.

10. The system of claim 9, wherein the desired time points include blood arrival to the vessel mask.

11. The system of claim 7, wherein the logic is applied to artery-specific data and further determines the relative blood volume flow rates from each feeding artery in well-mixed vessel segments.

12. The method of claim 7, wherein the logic assesses time points during which the simulated bolus data lies entirely within a vessel mask of interest to obtain estimates of the blood volume flow rate.

13. The method of claim 1, wherein the filling of the kinetic model derives parameter maps relating to blood volume, blood arrival time and dispersion of a blood bolus within the vessel mask.

14. The system of claim 7, wherein the logic that fits the kinetic model derives parameter maps relating to blood volume, blood arrival time and dispersion of a blood bolus within the vessel mask.

* * * * *